(12) United States Patent
Carroll et al.

(10) Patent No.: US 9,504,798 B2
(45) Date of Patent: Nov. 29, 2016

(54) HEADGEAR FOR MASK ASSEMBLY

(75) Inventors: Fiona Catherine Carroll, Five Dock (AU); Joel Edward Gibson, Balmain (AU); Errol Savio Alex D'Souza, Hornsby (AU); Bryony Louise Marshall, Westleigh (AU); Bruce Richard Davies, Strathfield (AU)

(73) Assignee: ResMed Limited, Bella Vista (AU)

( * ) Notice: Subject to any disclaimer, the term of this patent is extended or adjusted under 35 U.S.C. 154(b) by 49 days.

(21) Appl. No.: 13/617,274

(22) Filed: Sep. 14, 2012

(65) Prior Publication Data

US 2013/0008446 A1    Jan. 10, 2013

Related U.S. Application Data

(62) Division of application No. 11/922,475, filed as application No. PCT/AU2006/000968 on Jul. 7, 2006, now Pat. No. 8,286,635.

(60) Provisional application No. 60/697,365, filed on Jul. 8, 2005.

(51) Int. Cl.
*A61M 16/06* (2006.01)
*A62B 18/08* (2006.01)

(52) U.S. Cl.
CPC ........ *A61M 16/0683* (2013.01); *A62B 18/084* (2013.01); *Y10T 29/49826* (2015.01)

(58) Field of Classification Search
CPC ........................ A61M 16/0683; A62B 18/084
USPC ............ 128/201.22, 201.23, 205.25, 206.21, 128/206.27–207.11, 207.13; 2/9, 242, 422, 2/425, 452
See application file for complete search history.

(56) References Cited

U.S. PATENT DOCUMENTS

| | | | |
|---|---|---|---|
| 1,395,761 A | 11/1921 | Monro et al. | |
| 1,706,601 A | 3/1929 | Drager | |
| 2,353,643 A | 7/1944 | Bulbulian | |
| 3,457,564 A * | 7/1969 | Holloway | 2/8.1 |
| 5,481,763 A | 1/1996 | Brostrom et al. | |
| 5,542,128 A | 8/1996 | Lomas | |
| D383,204 S | 9/1997 | Lomas | |

(Continued)

FOREIGN PATENT DOCUMENTS

AU    199933172    12/1999
EP    1 020 201    7/2000

(Continued)

OTHER PUBLICATIONS

International Search Report for PCT/AU2006/000968 mailed Sep. 12, 2006.

(Continued)

*Primary Examiner* — Lynne Anderson
*Assistant Examiner* — Kathryn E Ditmer
(74) *Attorney, Agent, or Firm* — Nixon & Vanderhye P.C.

(57) ABSTRACT

A mask system for use between a patient and a structure to deliver a breathable gas to the patient includes a mask assembly including a frame, a cushion provided to the frame, and optionally an elbow provided to the frame. Headgear is removably attached to the mask assembly to maintain the mask assembly in a desired position on a patient's face. The headgear includes a top strap, crown straps which cooperate to form a round shape adapted to accommodate a crown of the patient's head, and bottom straps.

25 Claims, 19 Drawing Sheets

(56) References Cited

U.S. PATENT DOCUMENTS

| | | |
|---|---|---|
| 5,893,365 A | 4/1999 | Anderson |
| 6,112,746 A | 9/2000 | Kwok et al. |
| 6,148,817 A | 11/2000 | Bryant et al. |
| 6,269,814 B1 | 8/2001 | Blaszczykiewicz et al. |
| 6,418,929 B1 | 7/2002 | Norfleet |
| 6,805,117 B1 | 10/2004 | Ho et al. |
| D505,489 S | 5/2005 | Sleeper |
| D536,092 S | 1/2007 | Amarasinghe |
| 7,296,575 B1 * | 11/2007 | Radney .................... 128/207.11 |
| 7,779,832 B1 | 8/2010 | Ho |
| 2003/0051732 A1 | 3/2003 | Smith et al. |
| 2003/0172936 A1 * | 9/2003 | Wilkie et al. ............ 128/207.18 |
| 2004/0067333 A1 * | 4/2004 | Amarasinghe .................. 428/99 |
| 2004/0083534 A1 | 5/2004 | Ruiz et al. |
| 2004/0149280 A1 | 8/2004 | Semeniuk |
| 2005/0016535 A1 | 1/2005 | Smith et al. |
| 2005/0172969 A1 | 8/2005 | Ging et al. |
| 2006/0081252 A1 * | 4/2006 | Wood ...................... 128/207.11 |
| 2006/0283461 A1 * | 12/2006 | Lubke et al. ............ 128/207.11 |
| 2007/0175480 A1 | 8/2007 | Gradon et al. |
| 2007/0267023 A1 * | 11/2007 | Ging et al. ............... 128/206.21 |
| 2009/0211583 A1 | 8/2009 | Carrol et al. |
| 2011/0259337 A1 * | 10/2011 | Hitchcock et al. ...... 128/207.11 |

FOREIGN PATENT DOCUMENTS

| | | |
|---|---|---|
| WO | 98/48878 | 11/1998 |
| WO | 2004/012803 | 2/2004 |
| WO | 2005/063327 | 7/2005 |

OTHER PUBLICATIONS

Written Opinion of the International Searching Authority Sep. 12, 2006.

International Application No. PCT/AU2004/001813, filed Dec. 22, 2004, (p. 1 of specification, International Publication No. WO 2005/063327).

International Preliminary Report on Patentability for PCT/AU2006/000968 dated Jan. 9, 2008.

* cited by examiner

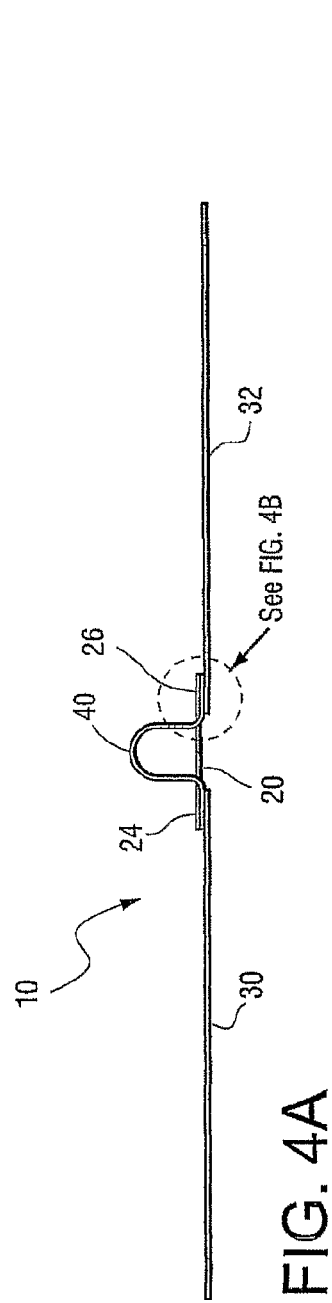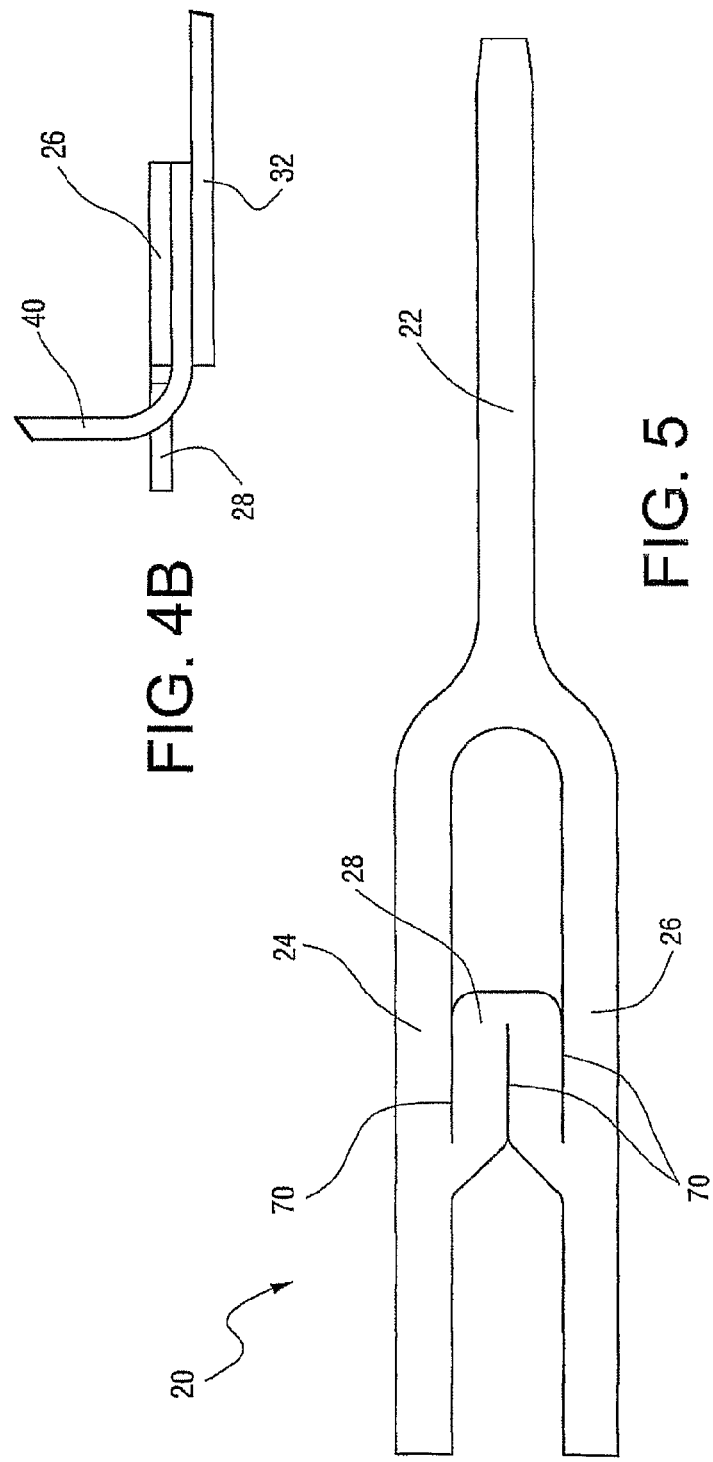

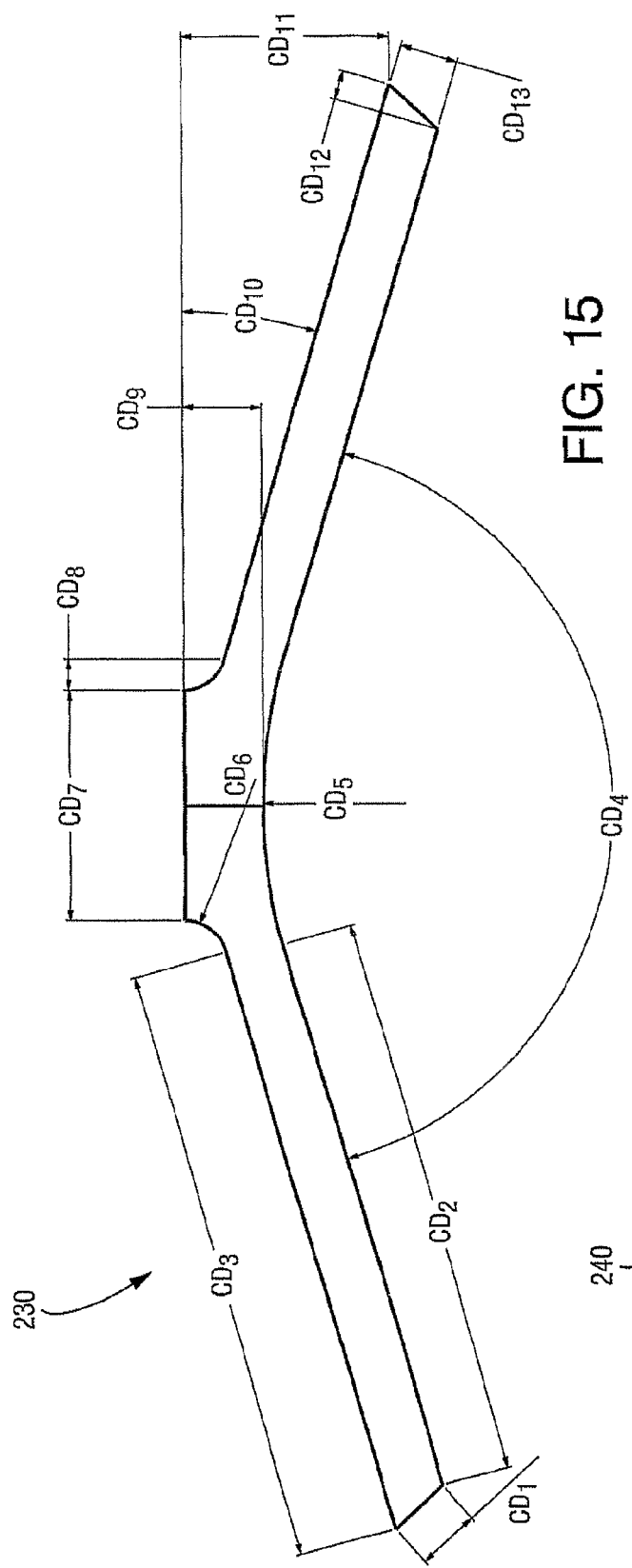
FIG. 15
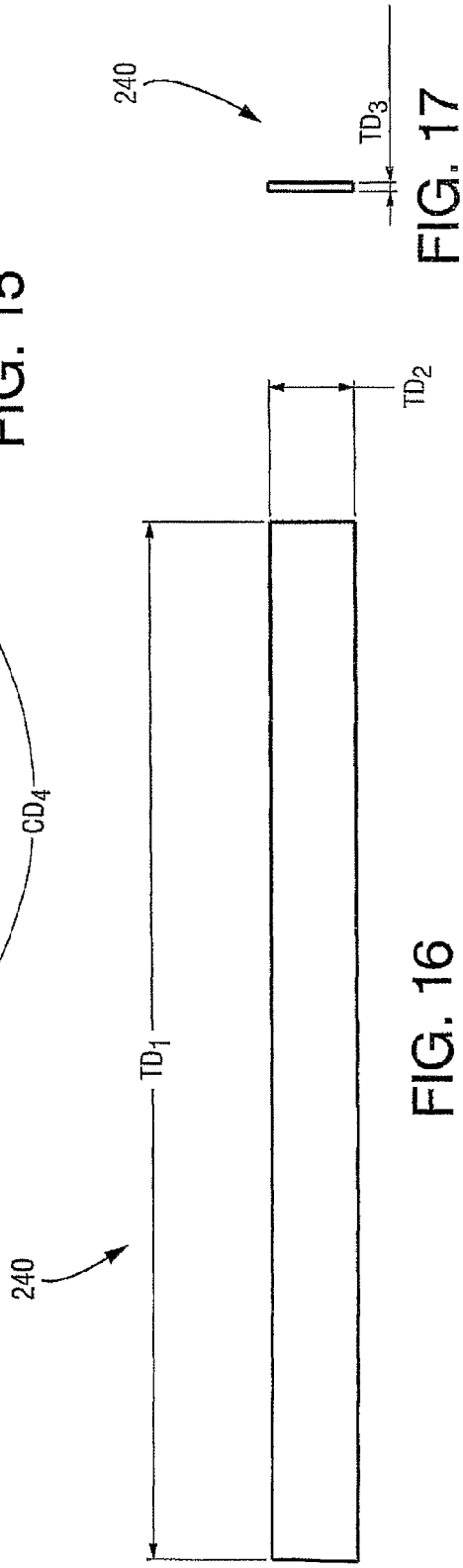
FIG. 16
FIG. 17

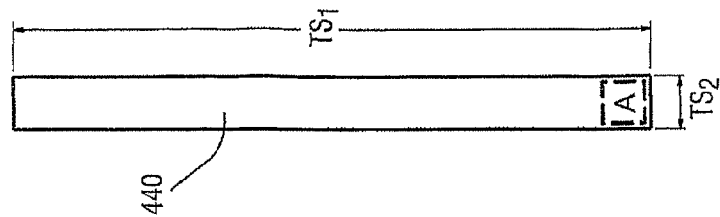
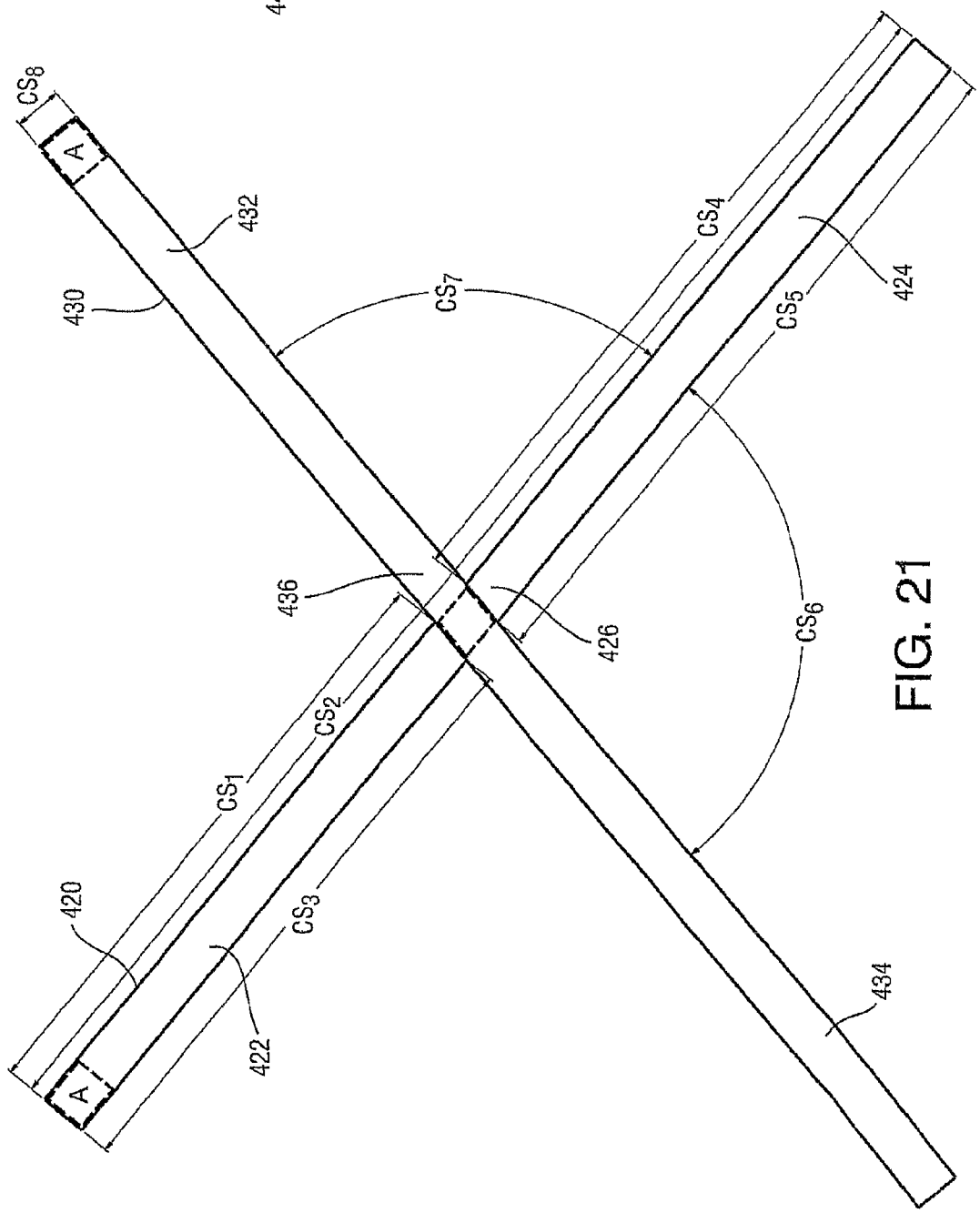

HEADGEAR FOR MASK ASSEMBLY

CROSS-REFERENCE TO APPLICATIONS

This application is a divisional of U.S. patent application Ser. No. 11/922,475, filed Dec. 19, 2007, which has been allowed and is the U.S. national phase of International Application No. PCT/AU2006/000968, filed Jul. 7, 2006, which designated the U.S. and claims the benefit of U.S. Provisional Application No. 60/697,365, filed Jul. 8, 2005, the entire contents of each of which are hereby incorporated by reference.

Also, PCT Application No. PCT/AU2004/001813, filed Dec. 22, 2004, is incorporated herein by reference, in its entirety.

FIELD OF THE INVENTION

The invention relates to headgear for use in holding a mask assembly in position on a patient's face, the mask assembly being used for Non-invasive Positive Pressure Ventilation (NPPV) and for continuous positive airway pressure (CPAP) therapy of sleep disordered breathing (SDB) conditions such as obstructive sleep apnea (OSA).

BACKGROUND OF THE INVENTION

Mask assemblies used for treatment of SDB such as OSA are typically held on a patient's head by headgear. Headgear typically includes one or more headgear straps that are adapted to engage with the mask assembly and hold the mask assembly in position on the patient's face. In addition, headgear should be comfortable so that a patient can wear the mask assembly at night while they sleep. There is a continuous need in the art for headgear that is comfortable, fits a wide range of patients, is easily manufactured, and is inexpensive.

SUMMARY OF THE INVENTION

One aspect of the invention relates to headgear that provides comfort and ease of adjustability to a wide range of patients.

Another aspect of the invention relates to headgear that provides a compact configuration to reduce material costs.

Another aspect of the invention relates to a mask system for use between a patient and a structure to deliver a breathable gas to the patient. The mask system includes a mask assembly including a frame and a cushion provided to the frame. Headgear is removably attached to the mask assembly to maintain the mask assembly in a desired position on a patient's face. The headgear includes a back headgear section providing a top strap, a pair of side straps attached to the back headgear section, and an elastic strap attached between the back headgear section and the pair of side straps.

Another aspect of the invention relates to headgear for use with a mask assembly. The headgear includes a back headgear section providing a top strap, a pair of side straps attached to the back headgear section, and an elastic strap attached between the back headgear section and the pair of side straps.

Another aspect of the invention relates to a method for forming headgear for a mask assembly. The method includes forming a back headgear section including a top strap adapted for connection to a top portion of the mask assembly, attaching a pair of side straps to the back headgear section adapted for connection to side portions of the mask assembly, and attaching an elastic strap between the back headgear section and the pair of side straps.

Another aspect of the invention relates to headgear for use with a mask assembly. The headgear includes a top strap, a bottom strap section including bottom straps and a connector, and a crown strap section including crown straps and a connector attached to the connector of the bottom strap section. Ends of the crown straps are attached to one another and to an end of the top strap. The crown straps cooperate to form a round shape or halo that is adapted to accommodate a crown of a patient's head.

Another aspect of the invention relates to headgear for use with a mask assembly. The headgear includes a top strap, a first strap section including a first crown strap, a first bottom strap, and a first connector, and a second strap section including a second crown strap, a second bottom strap, and a second connector. The second connector is attached to the first connector and ends of the first and second crown straps are attached to one another and to an end of the top strap. The first and second crown straps cooperate to form a round shape or halo that is adapted to accommodate a crown of a patient's head.

Another aspect of the invention relates to headgear for use with a mask assembly. The headgear includes a top strap, a first cross strap including a first crown strap portion, a first bottom strap portion, and a first connector portion, and a second cross strap including a second crown strap portion, a second bottom strap portion, and a second connector portion. The second connector portion is attached to the first connector portion so that the first and second cross straps extend transverse to one another. Ends of the first and second crown strap portions are attached to one another and to an end of the top strap. The first and second crown strap portions cooperate to form a round shape or halo that is adapted to accommodate a crown of a patient's head.

Another aspect of the invention relates to a method for forming headgear for a mask assembly. The method includes forming a bottom strap section including bottom straps and a connector, a crown strap section including crown straps and a connector, and a top strap; attaching the connector of the bottom strap section to the connector of the crown strap section; attaching ends of the crown straps to one another so that the crown straps cooperate to form a round shape or halo that is adapted to accommodate a crown of a patient's head; and attaching an end of the top strap to the ends of the crown straps.

Another aspect of the invention relates to a method for forming headgear for a mask assembly. The method includes forming a first strap section including a first crown strap, a first bottom strap, and a first connector, a second strap section including a second crown strap, a second bottom strap, and a second connector, and a top strap; attaching the first connector to the second connector; attaching ends of the first and second crown straps to one another so that the first and second crown straps cooperate to form a round shape or halo that is adapted to accommodate a crown of a patient's head; and attaching an end of the top strap to the ends of the first and second crown straps.

Another aspect of the invention relates to a method for forming headgear for a mask assembly. The method includes forming a first cross strap including a first crown strap portion, a first bottom strap portion, and a first connector portion, a second cross strap including a second crown strap portion, a second bottom strap portion, and a second connector portion, and a top strap; attaching the first connector portion to the second connector portion so that the first and second cross straps extend transverse to one another; attaching ends of the first and second crown strap portions to one another so that the first and second crown strap portions cooperate to form a round shape or halo that is adapted to accommodate a crown of a patient's head; and attaching an end of the top strap to the ends of the first and second crown strap portions.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 4A is a side view of the headgear shown in FIG. 2;

FIG. 4B is an enlarged view of a portion of the headgear shown in FIG. 4A;

FIG. 5 is a plan view of a back headgear section of the headgear shown in FIG. 2;

FIG. 15 is a plan view of a crown strap section of the headgear shown in FIG. 9 and showing dimensions of an embodiment;

FIGS. 16-17 are plan and side views of a top strap of the headgear shown in FIG. 9 and showing dimensions of an embodiment;

FIG. 21 is a partial assembled view of headgear according to yet another embodiment of the present invention, and showing dimensions of an embodiment;

FIG. 22 is a plan view of a top strap of the headgear shown in FIG. 21 and showing dimensions of an embodiment;

DETAILED DESCRIPTION OF ILLUSTRATED EMBODIMENTS

The figures illustrate headgear 10, 210, 310, 410 constructed according to embodiments of the present invention. In the illustrated embodiments, the headgear 10, 210, 310, 410 are adapted to be removably attached to a mask assembly 50 of the type described below to hold and maintain the mask assembly 50 in a desired position on a patient's face.

1. Mask Assembly

Figure 1:
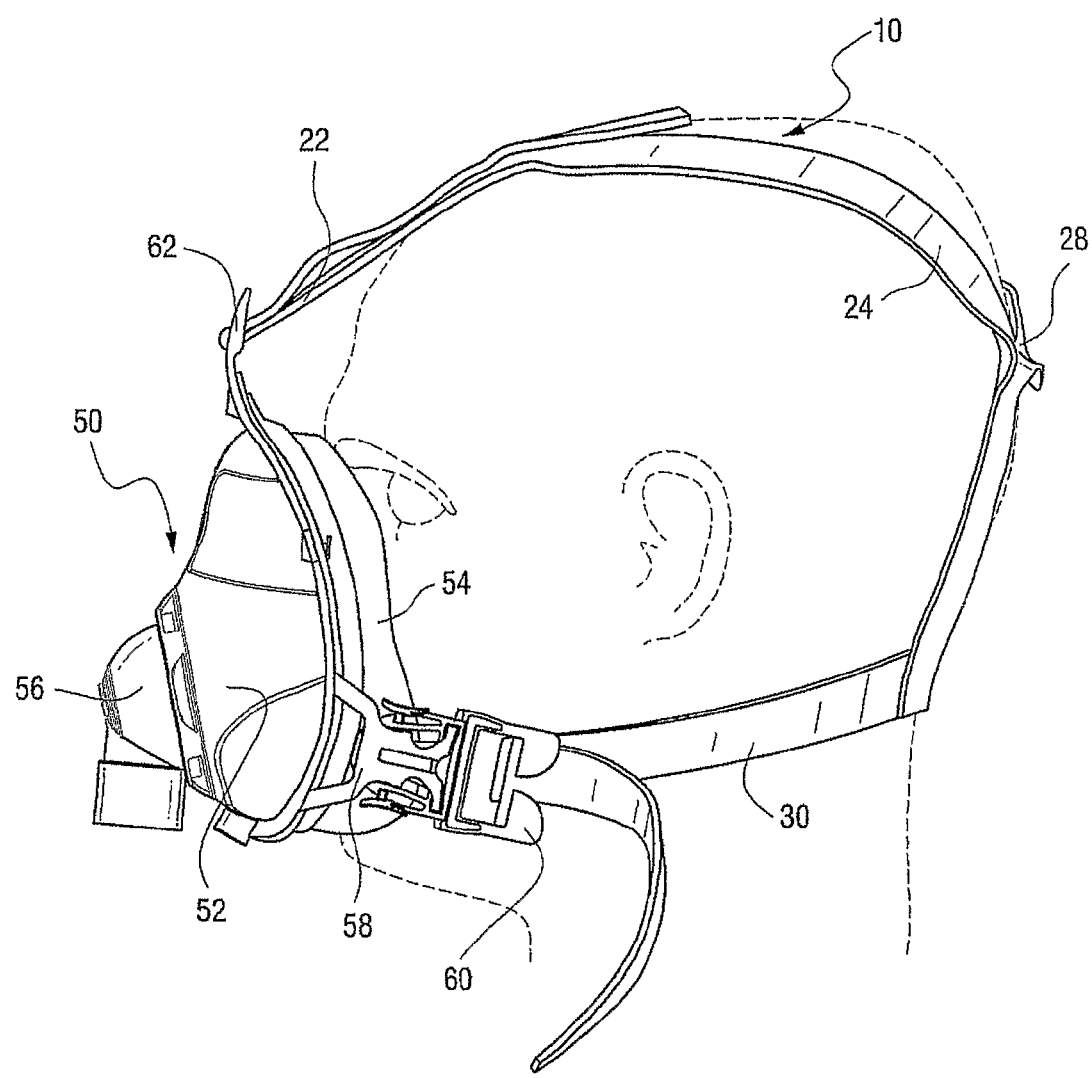
FIG. 1 is a side view of headgear constructed according to an embodiment of the present invention, the headgear in position on a patient's head to hold a mask assembly in position on a patient's face.
Figure 12:
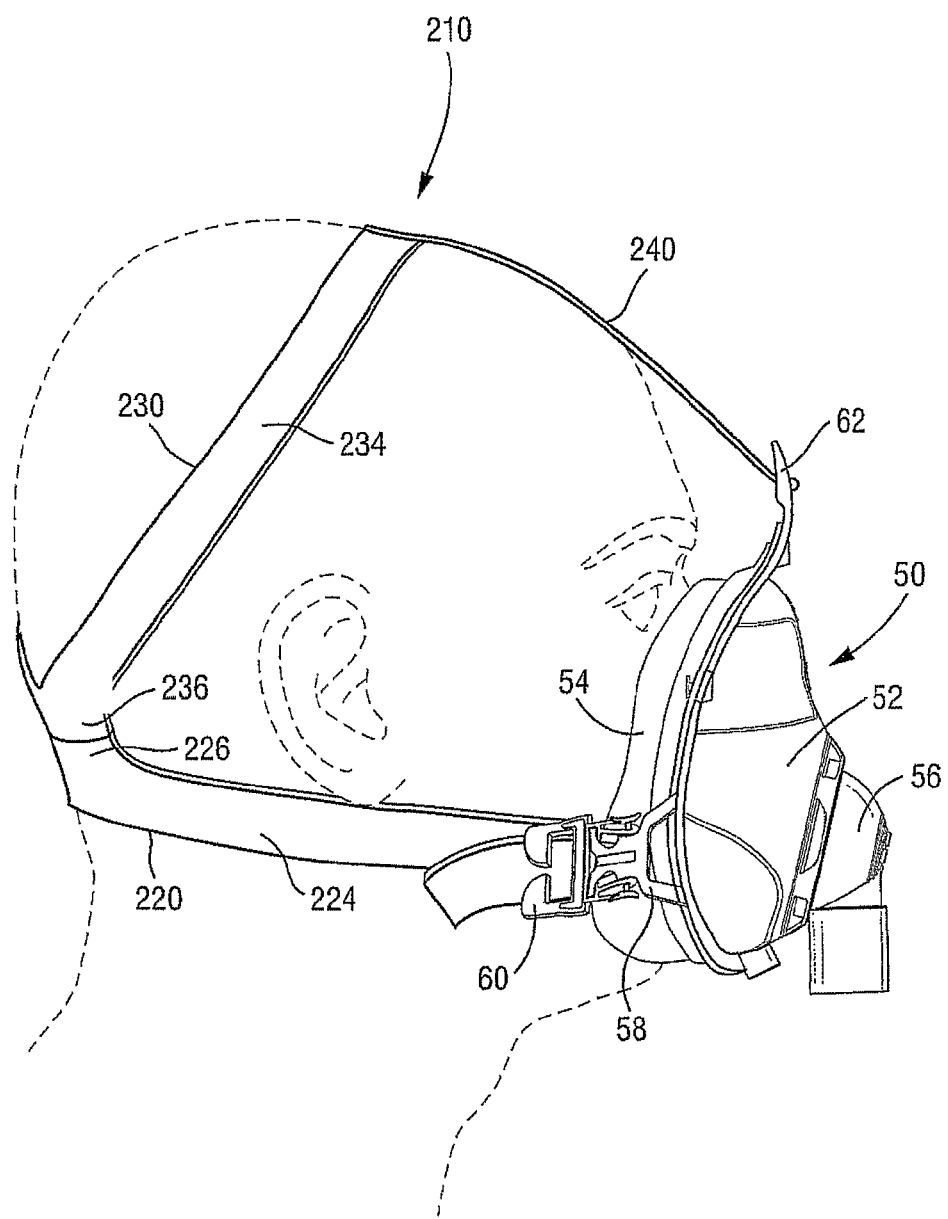
FIG. 12 is a side view of the headgear shown in FIG. 9 in position on a patient's head to hold a mask assembly in position on a patient's face.
Figure 24:
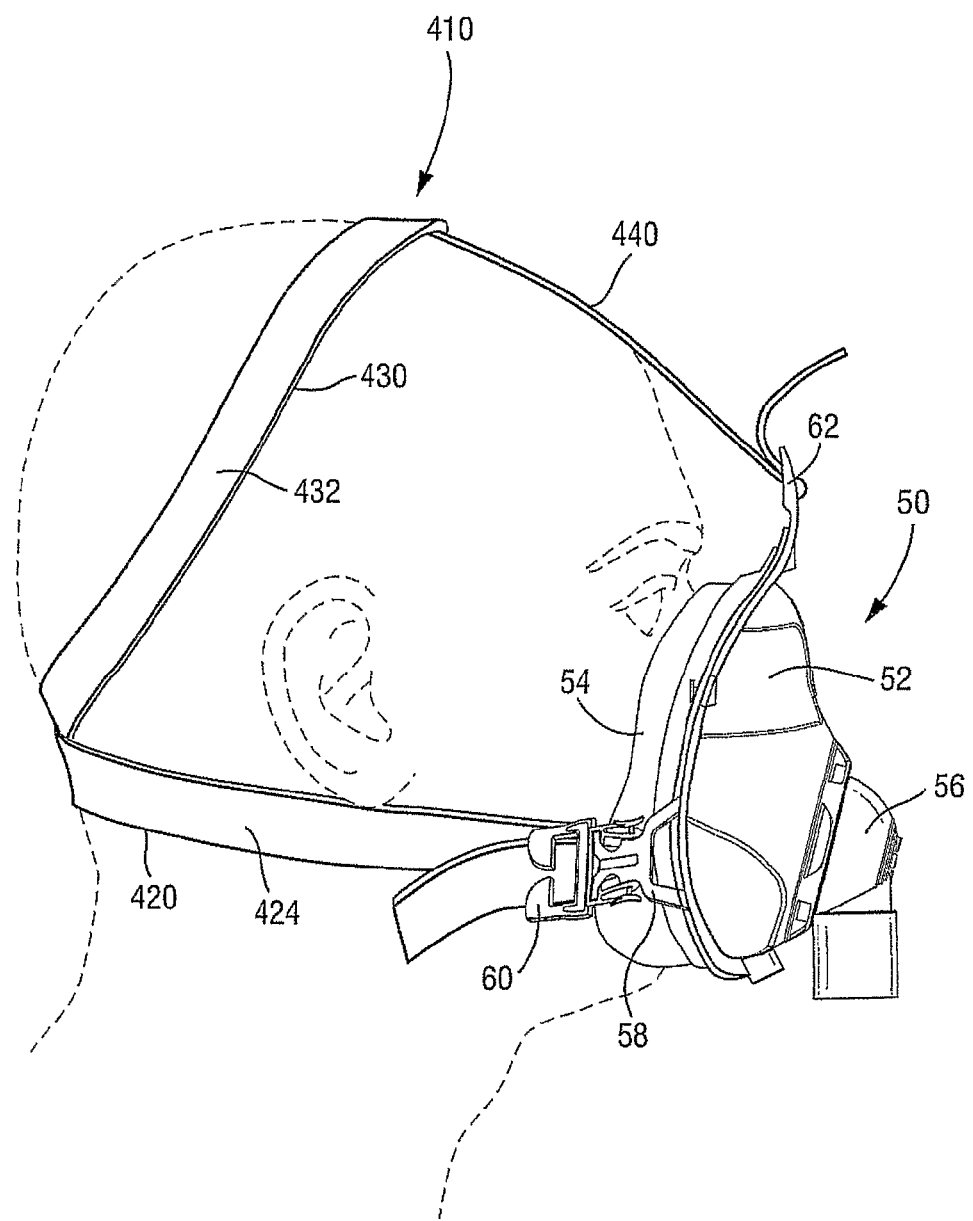
FIG. 24 is a side view of the headgear shown in FIG. 23 in position on a patient's head to hold a mask assembly in position on a patient's face.

As shown in FIGS. 1, 12, and 24 for example, the mask assembly 50 includes a frame 52 in the form of a shell, and a cushion 54 that is provided, e.g., attached, to the frame 52. A swivel elbow 56 is rotatably coupled or provided to the frame 52. The swivel elbow 56 is structured to be connected to an air delivery tube that delivers breathable gas to the patient, as is known in the art.

Side portions of the frame 52 include lateral outriggers 58 which support connector clip receptacles designed to receive connector clips 60 associated with the headgear 10, 210, 310, 410. A top portion of the frame 52 includes a centrally located upper extension 62 including various structure to interlock with a headgear strap of the headgear 10, 210, 310, 410.

Further details and embodiments of the mask assembly 50 are disclosed in PCT Application No. PCT/AU2004/001813, filed Dec. 22, 2004, the entirety incorporated herein by reference. While the headgear 10, 210, 310, 410 is described as being used with a mask assembly 50 of the type described above, it may be adapted for use with other suitable mask assemblies. That is, the mask assembly 50 is merely exemplary, and aspects of the headgear 10, 210, 310, 410 may be adapted for use with any suitable mask assembly, e.g., a full-face (oro-nasal) mask, a mouth (oro) mask, or a nasal mask.

2. First Illustrated Headgear Embodiment

FIGS. 1-8 illustrate headgear 10 according to an embodiment of the present invention. As shown in FIGS. 2, 3, 4A, and 4B, the headgear 10 includes an assembly of four parts. Specifically, the headgear 10 includes a back headgear section 20, a pair of side straps 30, 32, and an elastic strap 40. The back headgear section 20 includes a top strap 22, bottom straps 24, 26 extending from the top strap 22, and a connector strap 28 extending between intermediate portions of the bottom straps 24, 26.

In an embodiment, the back headgear section 20 may be manufactured by starting with a substantially flat piece of appropriate headgear material, such as polyester loop material, Breathoprene®, leather, cloth, plastic, etc., and then cutting, scoring or weakening the headgear material along predetermined cut lines to form the desired shape of the back headgear section 20 as shown in FIG. 5. The connector strap 28 may be created with a plurality of slits 70 that allow the strap 28 to expand in use to form open spaces as discussed below. The side straps 30, 32 may also be cut from a substantially flat piece of appropriate headgear material to form the desired shape of the side straps 30, 32. The elastic strap 40 may be cut or otherwise manufactured from a substantially flat piece of elastic material to form the desired shape of the elastic strap 40.

Figure 6:
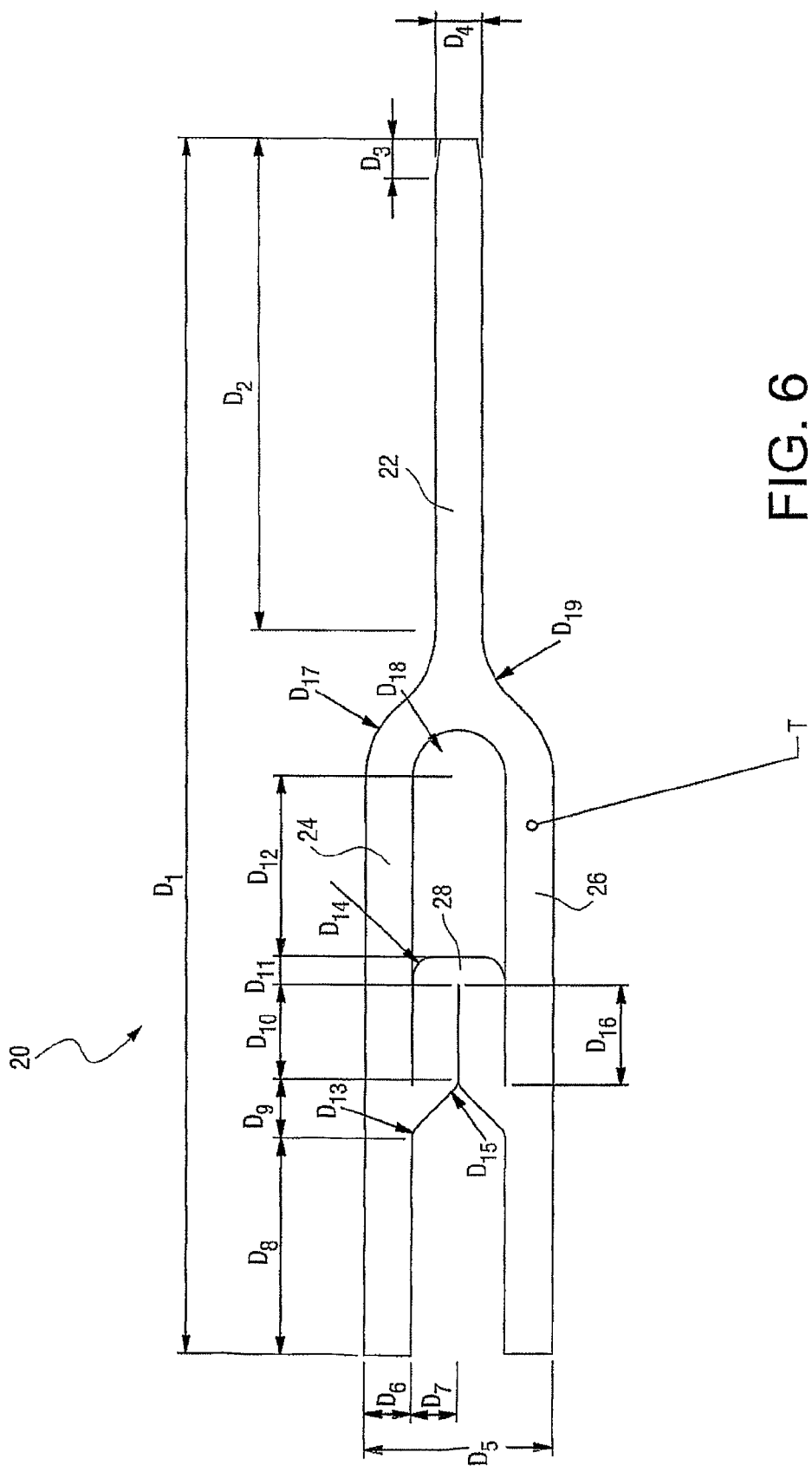
FIG. 6 is a plan view of the back headgear section shown in FIG. 5 and showing dimensions of an embodiment.

FIG. 5 illustrates the back headgear section 20, and FIG. 6 illustrates exemplary dimensions of an embodiment of the back headgear section 20. In an embodiment of the back headgear section 20 (as shown in FIG. 6), $D_1$ is 494 mm, $D_2$ is 200 mm, $D_3$ is 16 mm, $D_4$ is 19 mm, $D_5$ is 76 mm, $D_6$ is 19 mm, $D_7$ is 19 mm, $D_8$ is 87.5 mm, $D_9$ is 23.9 mm, $D_{10}$ is 38.4 mm, $D_{11}$ is 11.5 mm, $D_{12}$ is 73.5 mm, $D\_$is R6 mm, $D_{14}$ is R8 mm, $D_{15}$ is R6 mm, $D_{16}$ is 40.8 mm, $D_{17}$ is R38 mm, $D_{18}$ is R19 mm, and $D_{19}$ is R37 mm. The thickness T of the material, e.g., laminated material, may be 2.3±0.3 mm. In an embodiment, the material for the back headgear section 20 may be cut so that minimum elasticity is along the direction of the top strap 22.

Also, in an embodiment, the side straps 30, 32 may have a width similar to the width of the top strap 22 of the back headgear section 20, e.g., about 19 mm. Further, in an embodiment, the elastic strap 40 may be constructed of VELSTRECH® loop elastic and may have a length of about 130±5 mm. Although specific dimensions and ranges of the back headgear section 20, the side straps 30, 32, and the elastic strap 40 are indicated, it is to be understood that these dimensions and ranges are merely exemplary and other dimensions and ranges are possible depending on application. For example, the exemplary dimensions may vary by 10-20% or more or less depending on application.

The back headgear section 20, the side straps 30, 32, and the elastic strap 40 are attached to one another to form the headgear 10. As shown in FIGS. 2, 3, 4A, and 4B, ends of the elastic strap 40 are attached to respective ends of the bottom straps 24, 26 such that the elastic strap 40 extends between and transversely to the bottom straps 24, 26. Also, each side strap 30, 32 is attached to a respective end of the elastic strap 40 and a respective bottom strap 24, 26 such that each side strap 30, 32 extends transversely to the bottom straps 24, 26.

As best shown in FIG. 4B, the attachment area forms three layers of material, i.e., respective bottom strap 24, 26, elastic strap 40, and respective side strap 30, 32, and the three layers are attached to one another by stitching, e.g., a square-shaped stitch. However, the straps may be coupled to one another in any other suitable manner, e.g., glued, welded, or otherwise formed.

Figure 2:
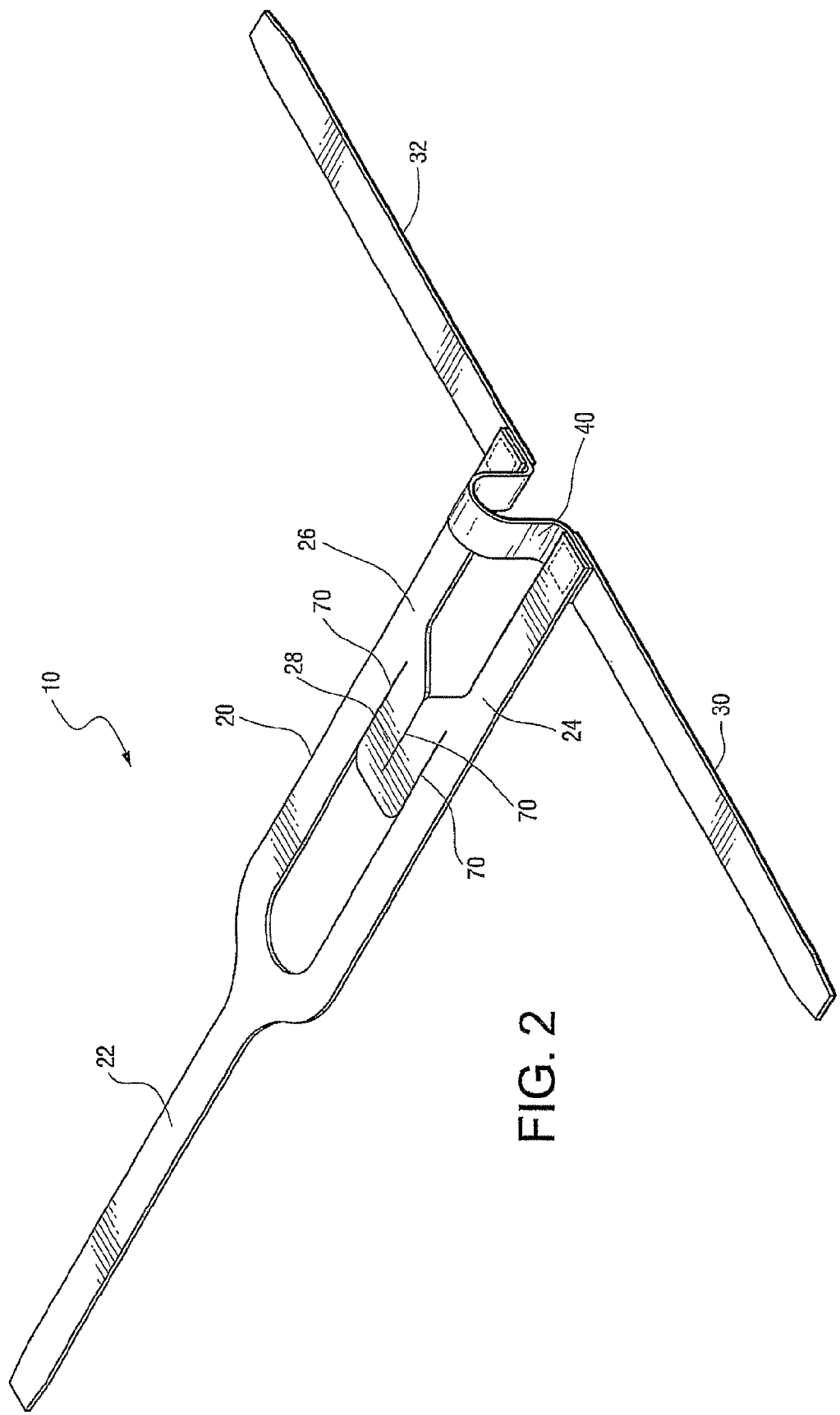
FIG. 2 is a perspective view of the headgear shown in FIG. 1 removed from the mask assembly and the patient's head.
Figure 3:
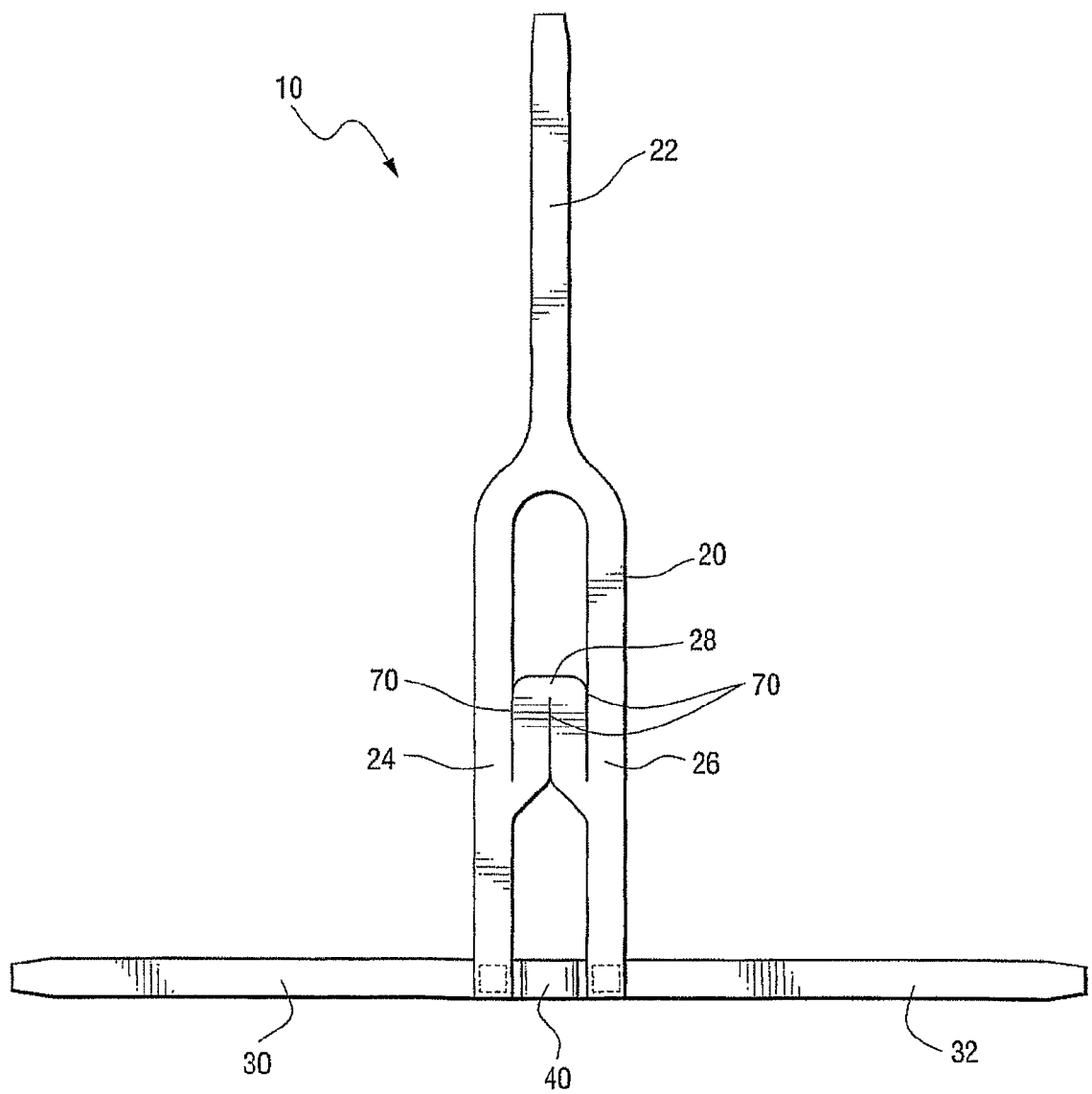
FIG. 3 is a top view of the headgear shown in FIG. 2.

Further, the elastic strap 40 has a length that is greater than a gap between the bottom straps 24, 26, as best shown in FIGS. 2 and 3. When the headgear 10 is in its flat configuration removed from the patient's head, the elastic strap 40 creates a fold due to its greater length. When the headgear 10 is on the patient's head, the elastic strap 40 will resiliently expand and conform to the patient's head as discussed below.

Figure 7:
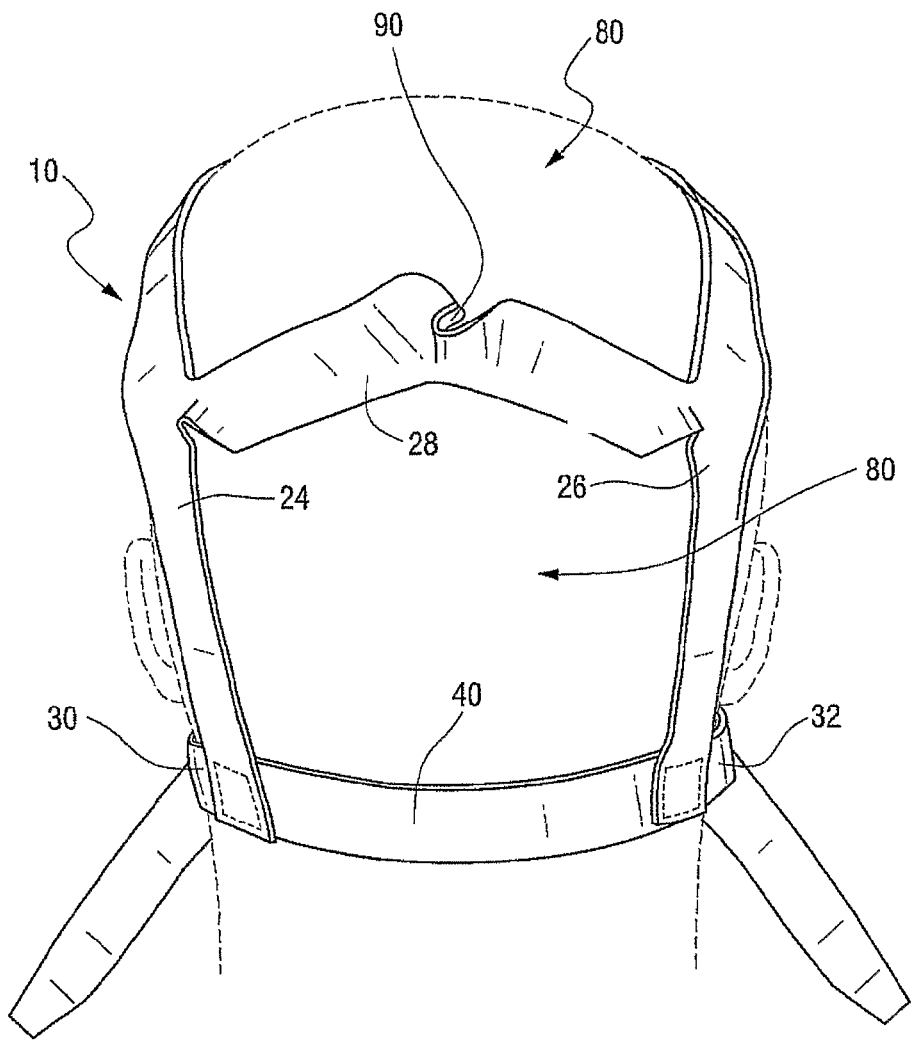
FIG. 7 is a rear view of the headgear shown in FIG. 1 in position on a patient's head.
Figure 8:
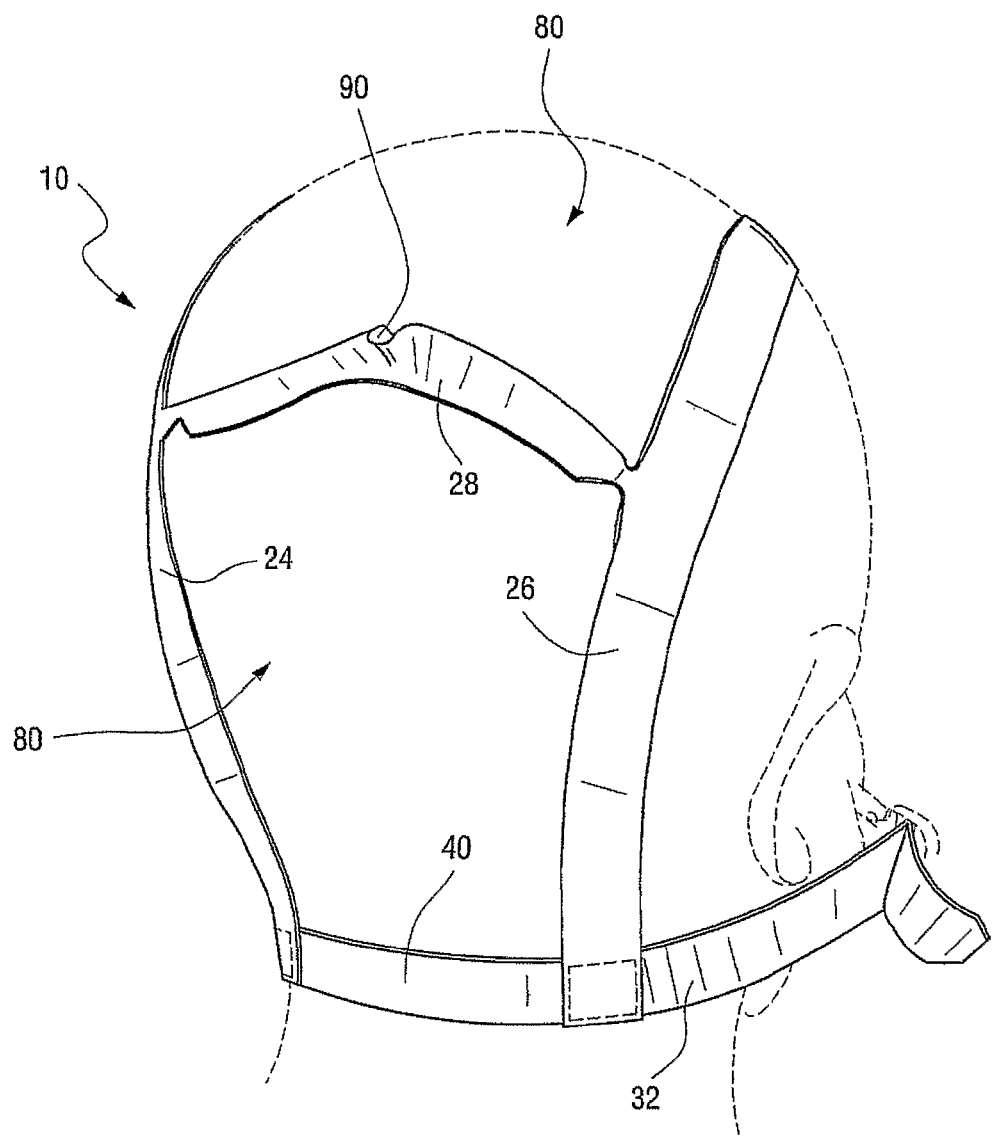
FIG. 8 is a rear perspective view of the headgear shown in FIG. 1 in position on a patient's head.

FIGS. 1, 7, and 8 illustrate the assembled headgear 10 attached to the mask assembly 50 and positioned on the patient's head. As illustrated, the headgear 10 is attached to the mask assembly 50 by attaching the top strap 22 to the centrally located upper extension 62 of the frame 52, and by attaching the side straps 30, 32 to respective connector clips 60 that are received in clip receptacles of the frame 52. Each of the upper extension 62 and connector clips 60 includes a crossbar that enables the end portion of the respective top strap 22 and side straps 30, 32 to be wrapped around in a known manner. However, the top strap 22 and side straps 30, 32 may be attached to the mask assembly 50 in other suitable manners.

In use, the connector strap 28 expands via the slits 70 and the elastic strap 40 expands via its elasticity to form a open spaces 80 when the headgear 10 is placed on the patient's head. As illustrated, the headgear 10 conforms to the shape of the patient's head and the connector strap 28 and upper portions of the bottom straps 24, 26 cup the occiput of the patient' head.

Also, the headgear 10 includes a fold lines 90 in at least the connector strap 28 which are created when the headgear 10 is positioned on the patient's head. Both the fold lines 90 and the elasticity of the elastic strap 40 helps to conform the headgear 10 to the patient's head.

2.1 Advantages of First Illustrated Headgear Embodiment

The configuration of headgear 10 provides several advantages. For example, the headgear configuration allows both the back headgear section 20 and the headgear side straps 30, 32 to be cut from a relatively small piece of flat headgear material. That is, the headgear configuration is relatively compact and is designed to expand along slits upon use by the patient. This arrangement reduces material costs.

This configuration also uses a relatively short elastic strap 40 which provides comfort and ease of adjustability to a wide range of head shapes, while not requiring a large expanse of relatively expensive elastic material. This arrangement also reduces material costs.

3. Alternative Headgear Embodiments

FIGS. 9-25 illustrate headgear 210, 310, 410 according to alternative embodiments of the present invention. In each embodiment, the headgear 210, 310, 410 includes an assembly of three parts and forms a round or halo shaped crown strap that accommodates or captures the crown of the patient's head.

3.1 First Alternative Headgear Embodiment

Figure 9:
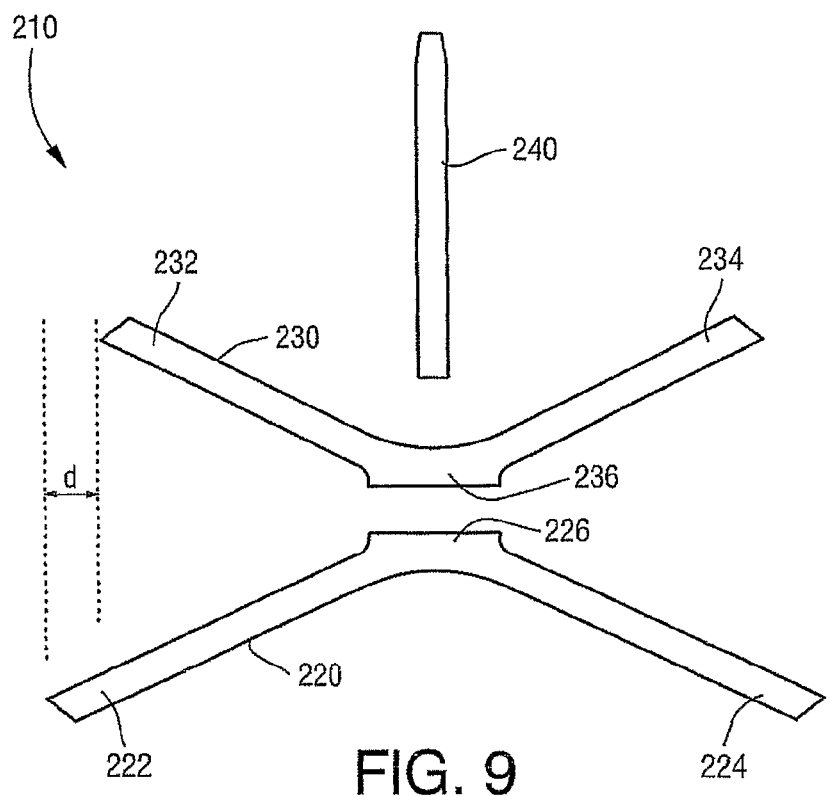
FIG. 9 is an exploded view of headgear according to another embodiment of the present invention.

FIGS. 9-17 illustrate headgear 210 according to another embodiment of the present invention. As best shown in FIG. 9, the headgear 210 includes an assembly of three parts. Specifically, the headgear 210 includes a bottom strap section 220, a crown strap section 230, and a top strap 240. The bottom strap section 220 includes bottom straps 222, 224 and a connector 226 between the bottom straps 222, 224. The crown strap section 230 includes crown straps 232, 234 and a connector 236 between the crown straps 232, 234. As illustrated, the crown straps 232, 234 are shorter than the bottom straps 222, 224, e.g., by a distance d.

Figure 10:
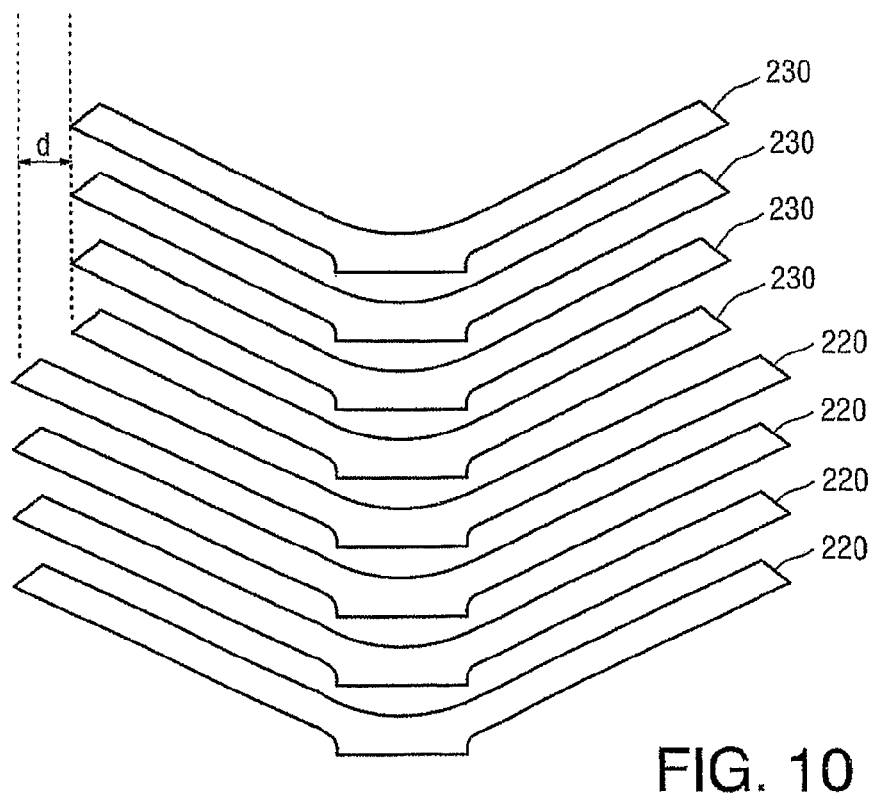
FIG. 10 illustrates a nesting arrangement for manufacturing the headgear shown in FIG. 9.

In an embodiment, the bottom strap section 220, the crown strap section 230, and the top strap 240 may be manufactured by starting with a substantially flat or 2-dimensional piece of appropriate headgear material, and then cutting, scoring or weakening the headgear material along predetermined cut lines (e.g., knife cut) to form the desired shape of the bottom strap section 220, the crown strap section 230, and the top strap 240. In an embodiment, multiple bottom and crown strap sections 220, 230 may be cut from the same piece of material. For example, FIG. 10 illustrates a nesting arrangement for forming multiple bottom and crown strap sections 220, 230 from the same piece of material. FIGS. 9 and 10 illustrate that the crown strap section 230 and the bottom strap section 220 have similar shapes.

Figure 11:
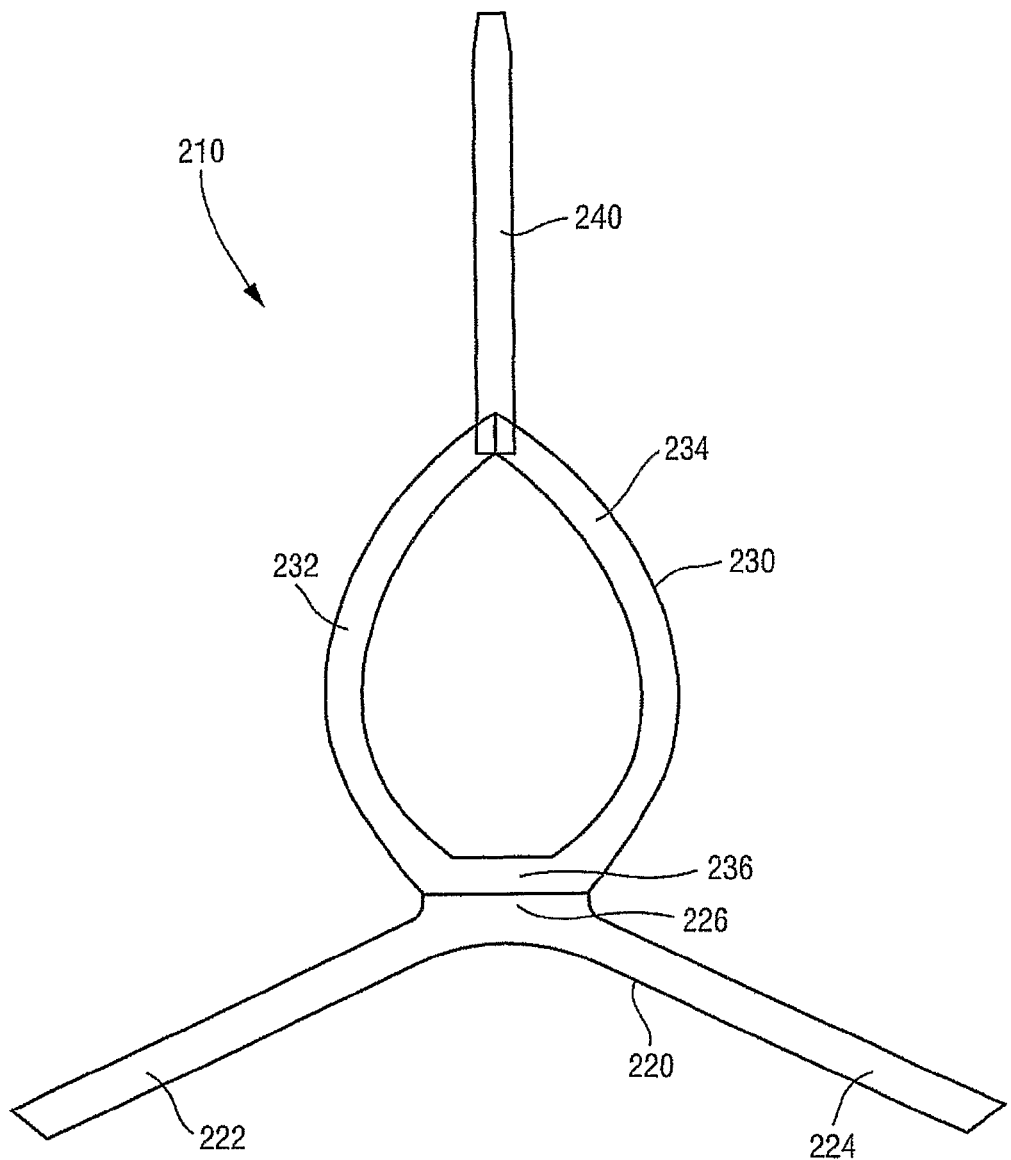
FIG. 11 is an assembled view of the headgear shown in FIG. 9.

The two-dimensional bottom strap section 220, crown strap section 230, and top strap 240 are attached to one another, e.g., stitched, welded, glued or otherwise formed, to form a three-dimensional headgear 210. Thus, the headgear 210 achieves a three-dimensional form from two-dimensional cut-out geometries. The three-dimensional form of the headgear 210 better conforms to the rounded shape of the patient' head. As shown in FIG. 11, the bottom and crown strap sections 220, 230 are attached by attaching ends of respective connectors 226, 236 to one another, e.g., along a generally horizontal seam line. Also, ends of the crown straps 232, 234 are attached to one another and attached to an end of the top strap 240. The crown straps 232, 234 cooperate to form a round-shape or halo that accommodates or captures the crown of the patient's head.

Figure 13:
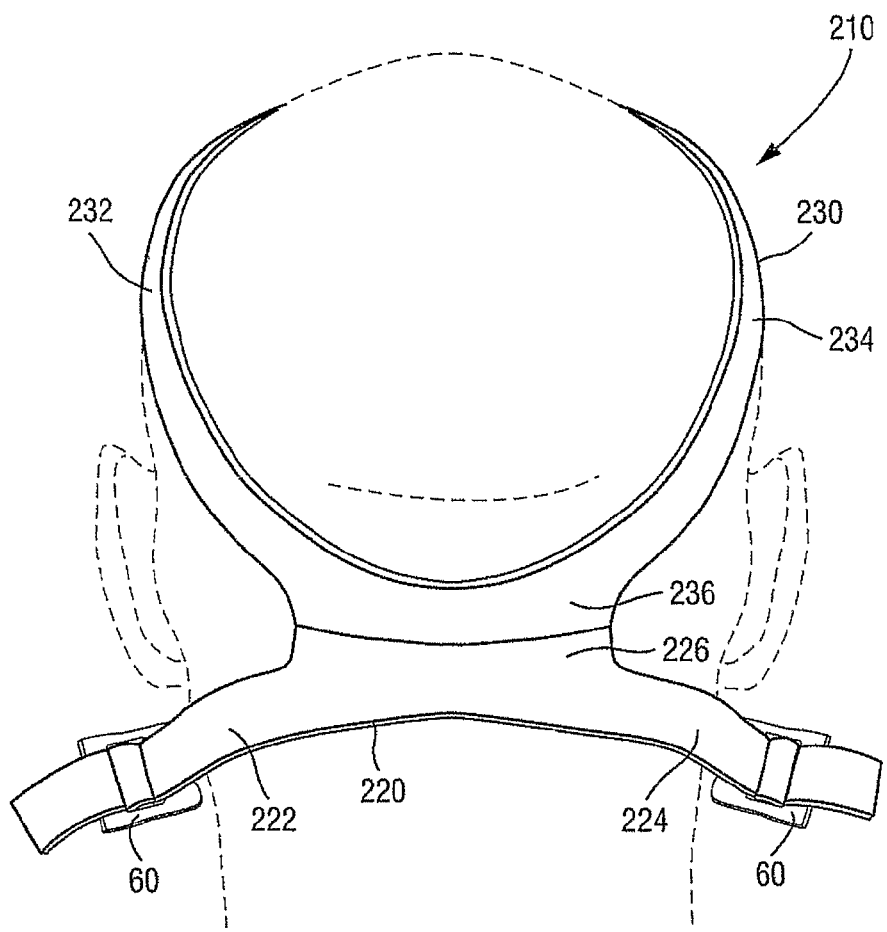
FIG. 13 is a rear view of the headgear shown in FIG. 9 in position on a patient's head to hold a mask assembly in position on a patient's face.

FIGS. 12 and 13 illustrate the assembled headgear 210 attached to the mask assembly 50 and positioned on the patient's head. As illustrated, the headgear 210 is attached to the mask assembly 50 at three points, e.g., by attaching the top strap 240 to the centrally located upper extension 62 of the frame 52 and by attaching the bottom straps 222, 224 to respective connector clips 60 that are received in clip receptacles of the frame 52. Each of the upper extension 62 and connector clips 60 includes a crossbar that enables the end portion of the respective top strap 240 and bottom straps 222, 224 to be wrapped around in a known manner. However, the top strap 240 and bottom straps 222, 224 may be attached to the mask assembly 50 in other suitable manners.

As illustrated, the headgear 210 conforms to shape of the patient's head and the crown straps 232, 234 form a halo that captures the crown or occiput of the patient's head. The crown strap arrangement provides stability for the headgear 210.

Figure 14:
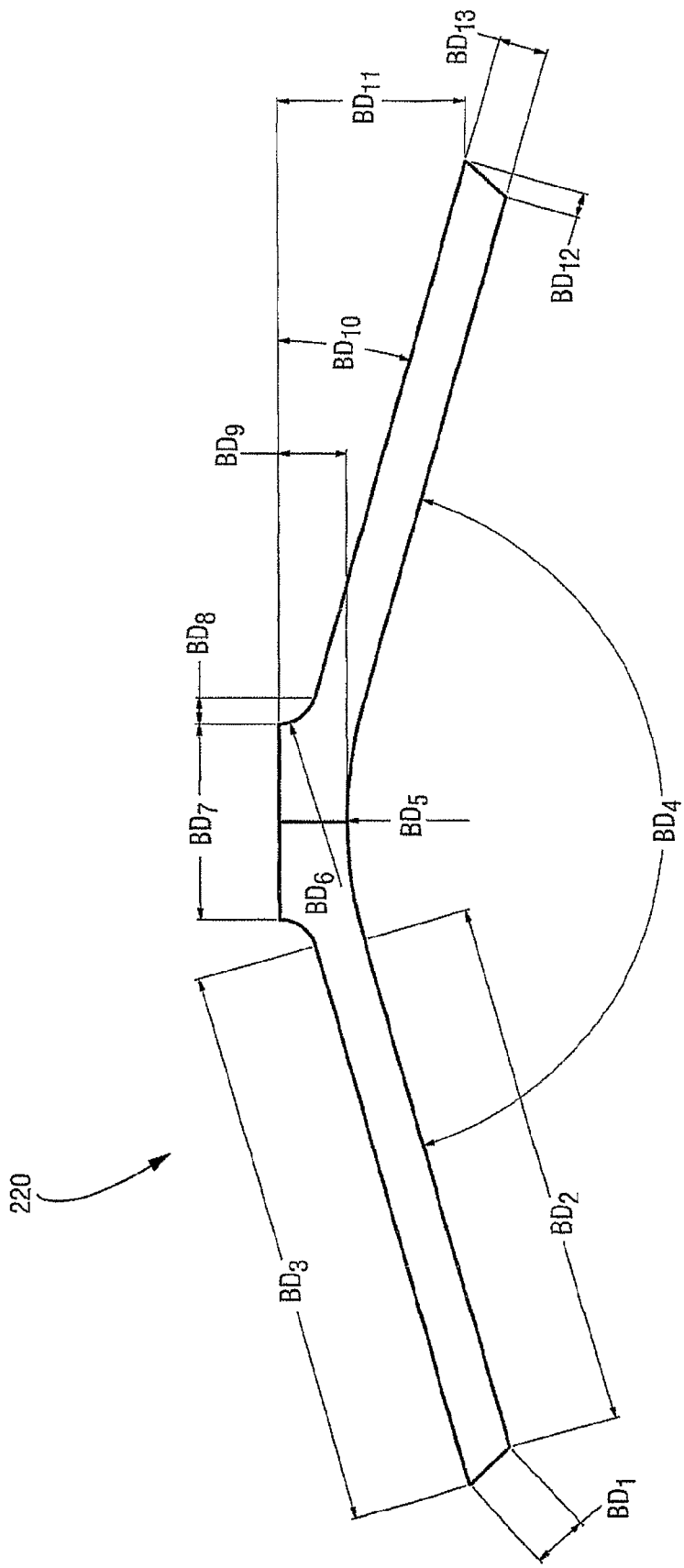
FIG. 14 is a plan view of a bottom strap section of the headgear shown in FIG. 9 and showing dimensions of an embodiment.

FIGS. 14-17 illustrate dimensions of an embodiment of the bottom strap section 220, the crown strap section 230, and the top strap 240. In an embodiment of the bottom strap section 220 (as shown in FIG. 14), $BD_1$ is 22.36 mm, $BD_2$ is 215.13 mm, $BD_3$ is 228.13 mm, $BD_4$ is 148.0°, $BD_5$ is R175.00 mm, $BD_6$ is R15.00 mm, $BD_7$ is 80.00 mm, $BD_8$ is 10.87 mm, $BD_9$ is 27.69 mm, $BD_{10}$ is 16.00°, $BD_{11}$ is 77.30 mm, $BD_{12}$ is 10.00 mm, and $BD\_$is 20.00 mm. In an embodiment of the crown strap section 230 (as shown in FIG. 15), $CD_1$ is 22.36 mm, $CD_2$ is 195.13 mm, $CD_3$ is 208.13 mm, $CD_4$ is 148.0°, $CD_5$ is R175.00 mm, $CD_6$ is R15.00 mm, $CD_7$ is 80.00 mm, $CD_8$ is 10.87 mm, $CD_9$ is 27.69 mm, $CD_{10}$ is 16.00°, $CD_{11}$ is 71.79 mm, $CD_{12}$ is 10.00 mm, and $CD\_$is 20.00 mm. In an embodiment of the top strap 240 (as shown in FIGS. 16 and 17), $TD_1$ is 240.00 mm, $TD_2$ is 20.00 mm, and $TD_3$ is 2.00 mm. Although specific dimensions are provided, it is to be understood that these dimensions are Merely exemplary and other dimensions are possible depending on application. For example, the exemplary dimensions may vary by 10-20% or more or less depending on application.

3.2 Second Alternative Headgear Embodiment

Figure 18:
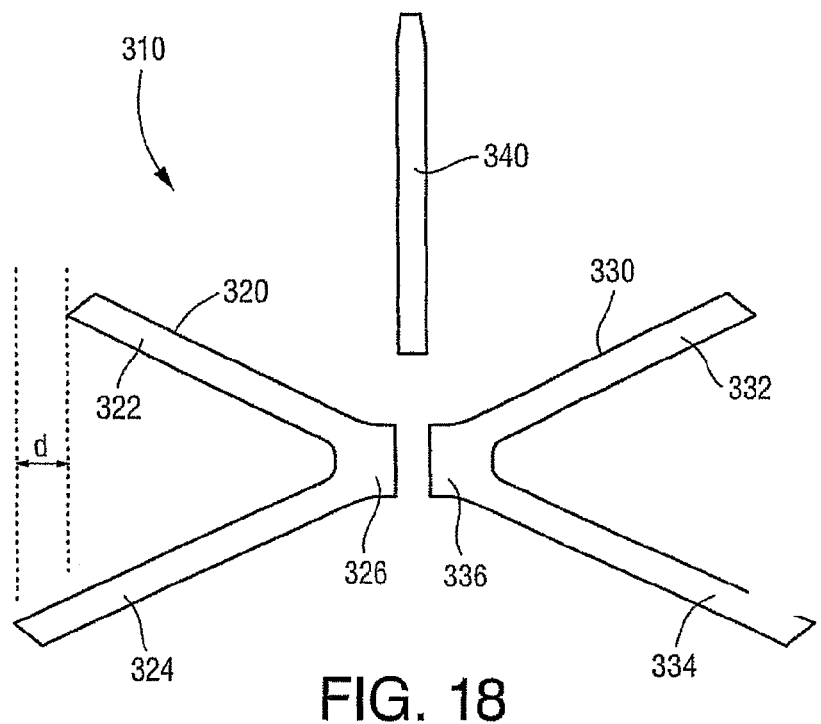
FIG. 18 is an exploded view of headgear according to another embodiment of the present invention.
Figure 19:
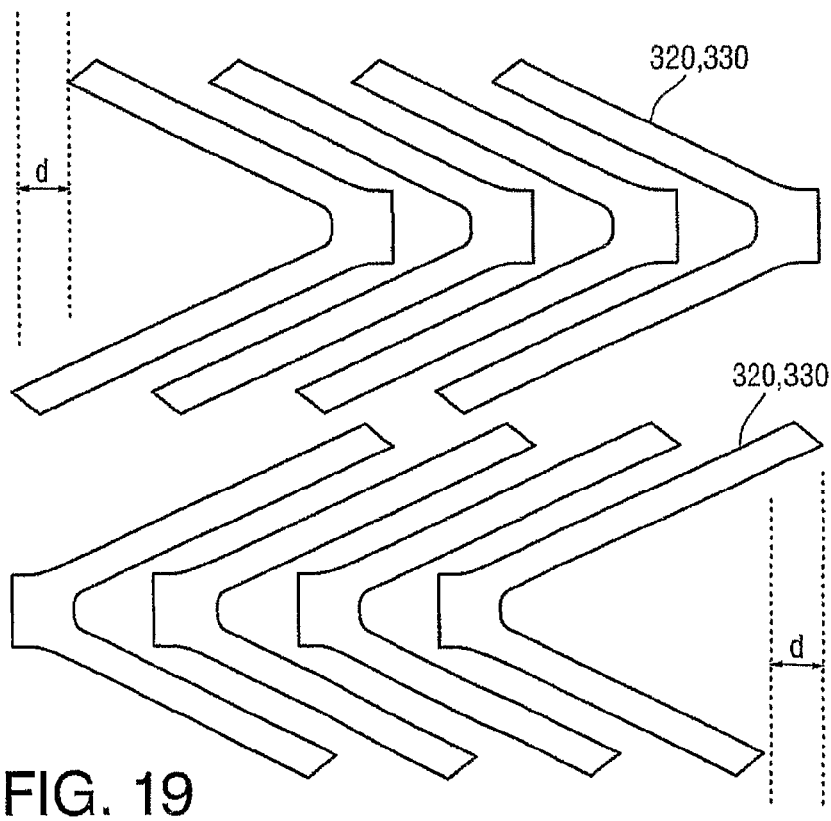
FIG. 19 illustrates a nesting arrangement for manufacturing the headgear shown in FIG. 18.
Figure 20:
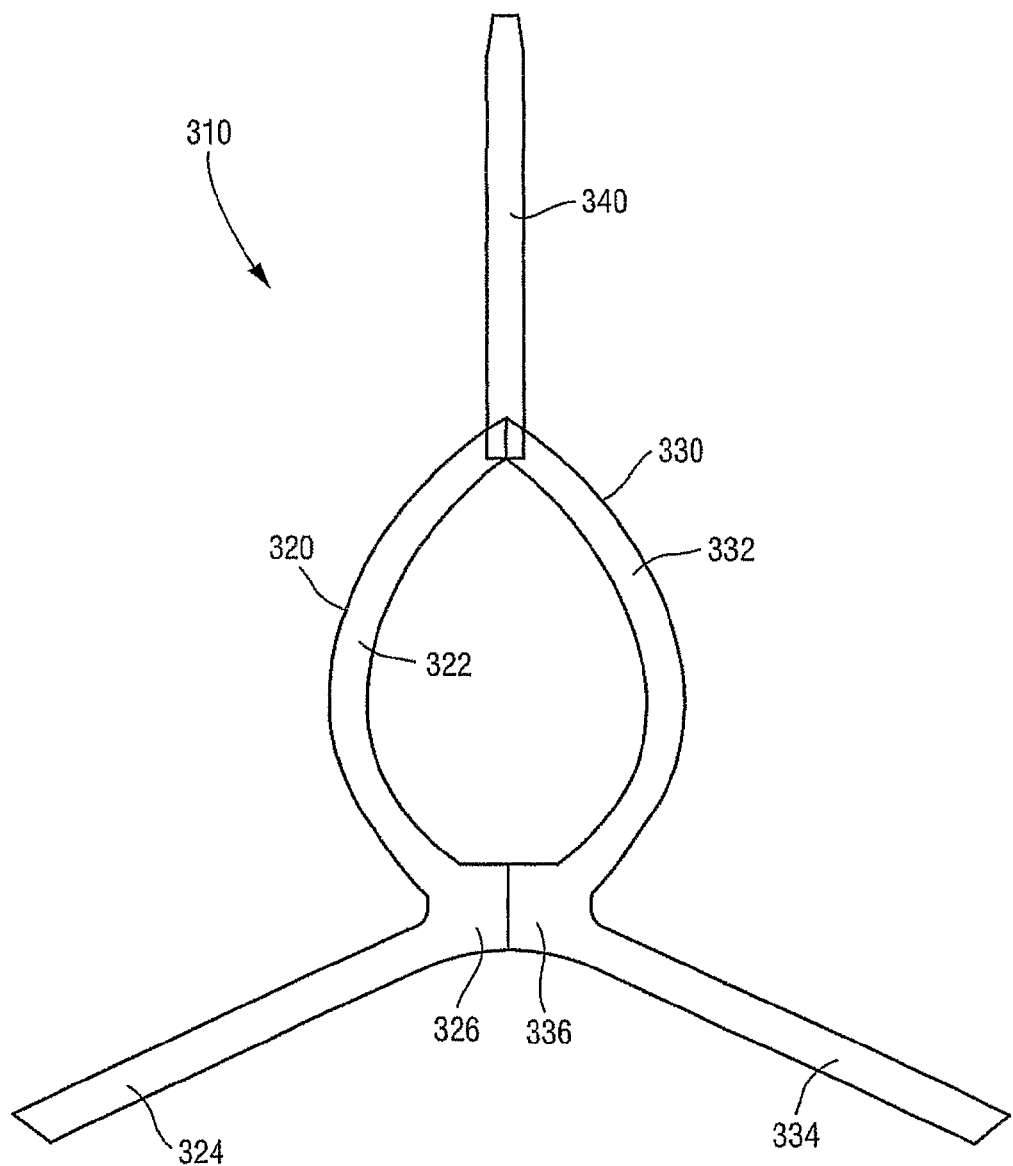
FIG. 20 is an assembled view of the headgear shown in FIG. 18.

FIGS. 18-20 illustrate headgear 310 according to another embodiment of the present invention. The headgear 310 in its assembled condition is substantially similar to the headgear 210 described above. In contrast, the assembled components of the headgear 310 are different.

As best shown in FIG. 18, the headgear 310 includes an assembly of three parts. Specifically, the headgear 310 includes a first strap section 320, a second strap section 330, and a top strap 340. The first strap section 320 includes a crown strap 322, a bottom strap 324, and a connector 326 between the straps 322, 324. The second strap section 330 includes a crown strap 332, a bottom strap 334, and a connector 336 between the straps 332, 334. As illustrated, the crown straps 322, 332 are shorter than the bottom straps 324, 334, e.g., by a distance d.

In an embodiment, the first strap section 320, the second strap section 330, and the top strap 340 may be manufactured by starting with a substantially flat or 2-dimensional piece of appropriate headgear material, and then cutting, scoring or weakening the headgear material along predetermined cut lines (e.g., knife cut) to form the desired shape of the first strap section 320, the second strap section 330, and the top strap 340. In an embodiment, multiple first and second strap sections 320, 330 may be cut from the same piece of material. For example, FIG. 19 illustrates a nesting arrangement for forming multiple first and second strap sections 320, 330 from the same piece of material. As illustrated, the first and second strap sections 320, 330 are mirror images of one another, and include the same structure and dimensions.

The two-dimensional first strap section 320, second strap section 330, and top strap 340 are attached to one another, e.g., stitched, welded, glued or otherwise formed, to form a three-dimensional headgear 310. Thus, the headgear 310 achieves a three-dimensional form from two-dimensional cut-out geometries. The three-dimensional form of the headgear 310 better conforms to the rounded shape of the patient' head. As shown in FIG. 20, the first and second strap sections 320, 330 are attached by attaching ends of respective connectors 326, 336 to one another, e.g., along a generally vertical seam line. Also, ends of the crown straps 322, 332 are attached to one another and attached to an end of the top strap 340. Similar to the headgear 210, the crown straps 322, 332 cooperate to form a round-shape or halo that accommodates or captures the crown of the patient's head.

The assembled headgear 310 may be attached to the mask assembly 50 and positioned on the patient's head in a manner as described above with respect to headgear 210, e.g., attaching the top strap 340 to the centrally located upper extension 62 and attaching the bottom straps 324, 334 to respective connector clips 60.

3.3 Third Alternative Headgear Embodiment

FIGS. 21-25 illustrate headgear 410 according to yet another embodiment of the present invention. As best shown in FIGS. 21 and 22, the headgear 410 includes an assembly of three parts. Specifically, the headgear 410 includes a first cross strap 420, a second cross strap 430, and a top strap 440. As illustrated, the first and second cross straps 420, 430 include the same structure and dimensions. The first cross strap 420 includes a crown strap portion 422, a bottom strap portion 424, and a connector portion 426 between the strap portions 422, 424. The second cross strap 430 includes a crown strap portion 432, a bottom strap portion 434, and a connector portion 436 between the strap portions 432, 434. As illustrated, the crown strap portions 422, 432 are shorter than the bottom strap portions 424, 434.

In an embodiment, the first cross strap 420, the second cross strap 430, and the top strap 440 may be manufactured by starting with a substantially flat or 2-dimensional piece of appropriate headgear material, and then cutting; scoring or weakening the headgear material along predetermined cut lines to form the desired shape of the first cross strap 420, the second cross strap 430, and the top strap 440.

Figure 23:
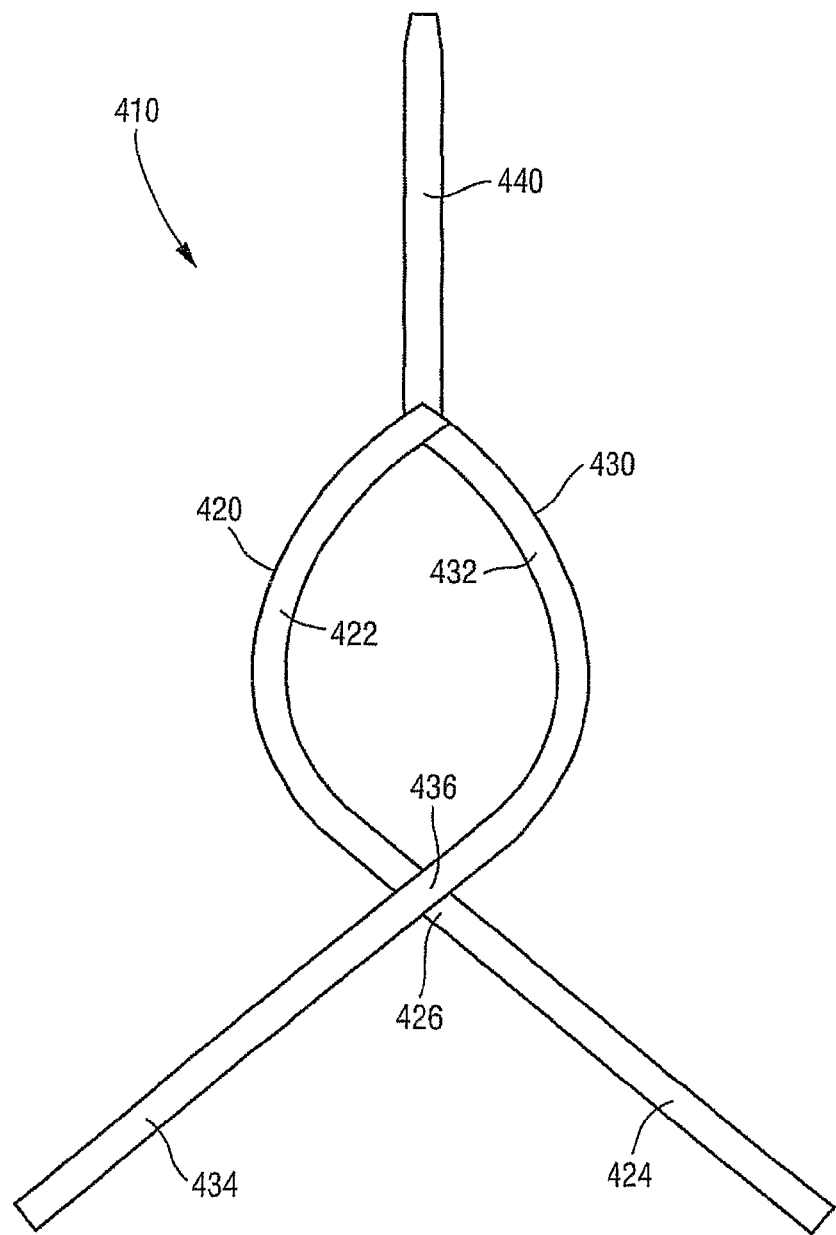
FIG. 23 is an assembled view of the headgear shown in FIGS. 21 and 22.

The two-dimensional first cross strap 420, second cross strap 430, and top strap 440 are attached to one another, e.g., stitched, welded, glued or otherwise formed, to form a three-dimensional headgear 410. Thus, the headgear 410 achieves a three-dimensional form from two-dimensional cut-out geometries. The three-dimensional form of the headgear 410 better conforms to the rounded shape of the patient' head. As shown in FIG. 23, the first and second cross straps 420, 430 are attached by attaching respective connector portions 426, 436 to one another so that the first and second cross straps 420, 430 extend transverse to one another. The connector portion 426 may pass under or over the connector portion 436 (e.g., FIGS. 21 and 23 show the connector portion 426 passing under the connector portion 436). Also, ends of the crown strap portions 422, 432 are attached to one another and attached to an end of the top strap 440 (e.g., attach A to A to A of the crown strap portions 422, 432 and top strap 440 as shown in FIGS. 21 and 22). Similar to the headgear 210 and 310, the crown strap portions 422, 432 cooperate to form a round-shape or halo that accommodates or captures the crown of the patient's head.

Figure 25:
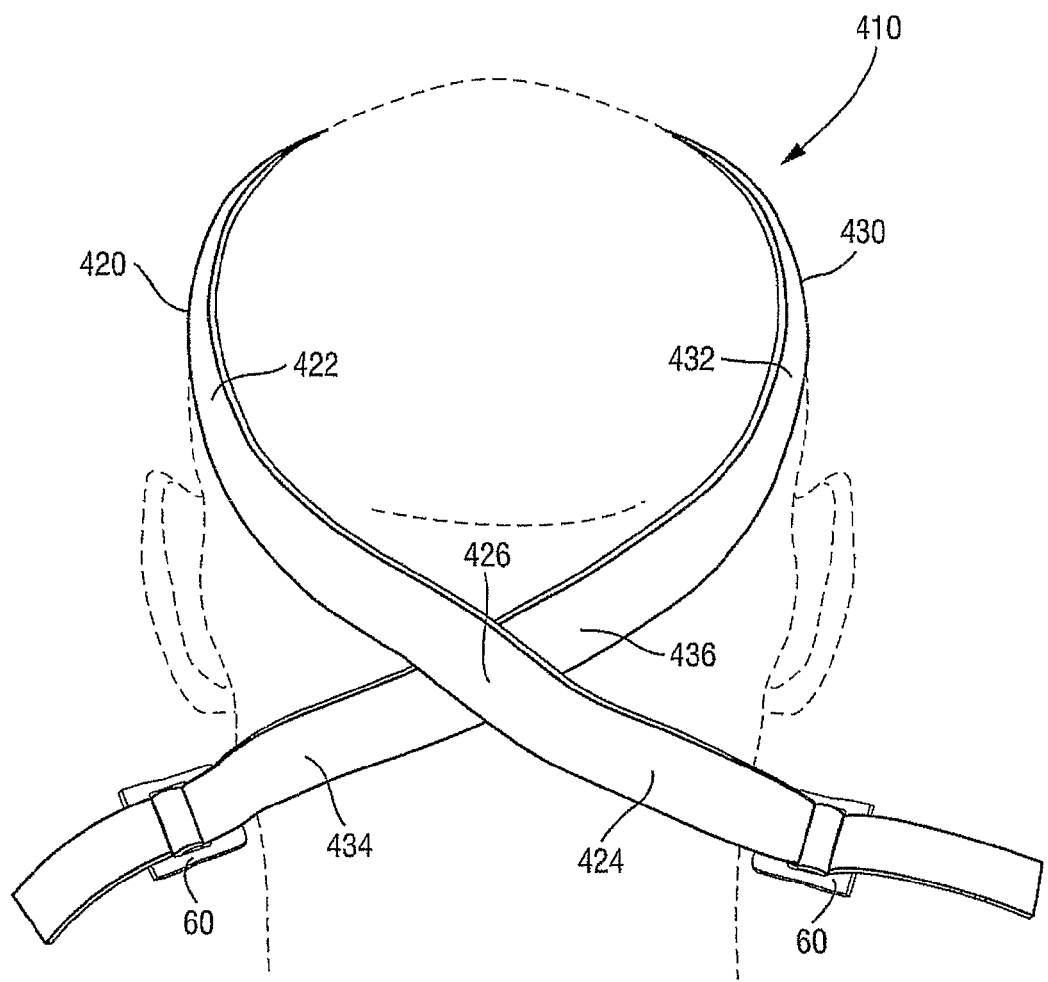
FIG. 25 is a rear view of the headgear shown in FIG. 23 in position on a patient's head to hold a mask assembly in position on a patient's face.

FIGS. 24 and 25 illustrate the assembled headgear 410 attached to the mask assembly 50 and positioned on the patient's head. As illustrated, the headgear 410 is attached to the mask assembly 50 at three points, e.g., by attaching the top strap 440 to the centrally located upper extension 62 of the frame 52 and by attaching the bottom strap portions 424, 434 to respective connector clips 60 that are received in clip receptacles of the frame 52.

As illustrated, the headgear 410 conforms to shape of the patient's head and the crown strap portions 422, 432 form a halo that captures the crown or occiput of the patient's head. The crown strap arrangement provides stability for the headgear 410.

FIGS. 21 and 22 also illustrate dimensions of an embodiment of the first and second cross straps 420, 430 and the top strap 440. In an embodiment of the cross straps 420, 430 (as shown in FIG. 21), $CS_1$ is 256 mm, $CS_2$ is 570 mm, $CS_3$ is 252 mm, $CS_4$ is 293.6 mm, $CS_5$ is 297.6 mm, $CS_6$ is 101.3°, $CS_7$ is 78.7°, and $CS_8$ is 20 mm. In an embodiment of the top strap 440 (as shown in FIG. 22), $TS_1$ is 240 mm and $TS_2$ is 20 mm. Although specific dimensions are provided, it is to be understood that these dimensions are merely exemplary and other dimensions are possible depending on application. For example, the exemplary dimensions may vary by 10-20% or more or less depending on application.

3.4 Advantages of Alternative Headgear Embodiments

The configuration of headgear 210, 310, 410 provide several advantages. For example, the force vector generated from the top strap 240, 340, 440 acts to pull together the Crown straps 232, 234, 322, 332, 422, 432 that define the halo. This arrangement cups the patient's head better and prevents the crown straps from tending to slide downwards over the patient's head. When viewed from the side (e.g., see FIGS. 12 and 24), the crown straps lie on the top and back of the patient's head, which provides a vertical and horizontal reaction force to headgear strap tension.

Various head shapes (e.g., ball and egg/pointed) are accommodated for as the crown of the patient's head partially extends through the hole defined by the halo-shaped crown straps. In an embodiment, the halo-shaped crown straps immediately capture the crown of the patient's head when first fitted to the patient. This arrangement minimizes the time required by busy nurses to fit the mask to the patient.

In an embodiment, one headgear design and size may be provided for small, medium, and large sized masks, e.g., full-face masks such as mask assembly 50.

The circumferential length of the crown straps may be sized so that it fits the smallest head (e.g., $5^{th}$ percentile) in the total adult male and female population without the head being able to pass through the halo-shaped crown straps. Also, the circumferential length of the crown straps may take into account elasticity and creep in the headgear material.

In an embodiment, the elasticity and creep properties of the headgear material of the headgear 210, 310, 410 may be characterised to suit both vented and non-vented disposable full-face masks. Therefore, a common headgear design may be used for both vented and non-vented masks.

Due to higher air pressures (e.g., greater than 30 $cmH_2O$), non-vented masks produce more mask bounce onto the patient's face due to the pressure swings during the inhalation and exhalation cycle. In known embodiments, vented mask headgear have been fabricated from an elastic material (e.g., AccuMED Breath-O-Prene) and non-vented mask headgear have had a non-extensible strap sewn into the headgear to eliminate elasticity and mask bounce. The headgear material according to embodiments of headgear 210, 310, 410 may have minimal elasticity, thereby making the headgear suitable for both the vented and non-vented masks, e.g., hospital disposable full-face masks. Examples of headgear material for headgear 210, 310, 410 may include polyester, nylon, and foam.

In an embodiment, the elasticity of the headgear material of headgear 210, 310, 410 may be selected such that it provides up to about 65 mm of displacement for forces up to about 0.02 kN. In one acceptable range, the elasticity of the headgear material of the headgear 210, 310, 410 may be selected such that it provides up to about 20 mm of displacement for forces up to about 0.02 kN. In a preferred range, the elasticity of the headgear material of headgear 210, 310, 410 may be selected such that it provides up to about 14 mm of displacement for forces up to about 0.02 kN. In another preferred range, the elasticity of the headgear material of headgear 210, 310, 410 may be selected such that it provides between about 4 mm and about 14 mm of displacement for forces up to about 0.02 kN.

Other advantages of the headgear configuration include a reduction in material waste to increase yield (e.g., nesting arrangement during manufacturing), and the consideration of a range of low cost fabric alternatives. The headgear lifespan may improve due to headgear material that has less creep and adequate strap lengths to cover anthropometric ranges. Also, the headgear has improved structural form when removed from packaging, a simplistic design to minimize confusion, and headgear material that has an overall softer look with a higher quality finish. In addition, the structural form of the headgear makes the headgear intuitive to fit onto the patient. The "halo" feature and padded neck-piece are cognitive devices, and the "halo" feature immediately captures the crown of the patient's head, which centers the headgear.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. Headgear for use with a mask assembly, comprising:
a top strap;
a one-piece bottom strap section including bottom straps and a first connector; and
a one-piece crown strap section including a pair of crown straps and a second connector attached to the first connector, the crown straps cooperating to form a round shape or halo that is adapted to accommodate a crown of a patient's head, each crown strap including a first end, the first ends of the crown straps being directly attached to one another and to a first end of the top strap, a second end of the top strap being configured to attach to a mask assembly,
wherein, in a flat, pre-assembled state, the crown straps each extend straight from the second connector to the respective first ends of the crown straps.

2. The headgear according to claim 1, wherein the crown straps are shorter than the bottom straps.

3. The headgear according to claim 1, wherein the top strap, bottom strap section, and crown strap section are constructed from a substantially flat or 2-dimensional piece of material, and attached to one another to achieve a 3-dimensional form.

4. The headgear according to claim 1, wherein the bottom straps are straight in the flat, pre-assembled state and an angle defined by the bottom straps in the flat, pre-assembled state is the same as an angle defined by crown straps in the flat, pre-assembled state.

5. A mask system for use between a patient and a structure to deliver a breathable gas to the patient, the mask system comprising:
a mask assembly including a frame and a cushion provided to the frame; and
headgear according to claim 1.

6. Headgear for use with a mask assembly, comprising:
a top strap;
a one-piece first strap section including a first crown strap, a first bottom strap, and a first connector; and
a one-piece second strap section including a second crown strap, a second bottom strap, and a second connector, the second connector being attached to the first connector and ends of the first and second crown straps being directly attached to one another and to an end of the top strap,
wherein the first and second crown straps cooperate to form a round shape or halo that is adapted to accommodate a crown of a patient's head, and
wherein, in a flat, pre-assembled state, the first crown strap extends straight from the first connector to the end of the first crown strap and the second crown strap extends straight from the second connector to the end of the second crown strap.

7. The headgear according to claim 6, wherein the first and second crown straps are shorter than the first and second bottom straps.

8. The headgear according to claim 6, wherein the top strap, first strap section, and second strap section are constructed from a substantially flat or 2-dimensional piece of material, and attached to one another to achieve a 3-dimensional form.

9. Headgear for use with a mask assembly, comprising:
a top strap;
a one-piece first cross strap including a first crown strap portion, a first bottom strap portion, and a first connector portion; and
a one-piece second cross strap including a second crown strap portion, a second bottom strap portion, and a second connector portion, the second connector portion being attached to the first connector portion so that the first and second cross straps extend transverse to one another and ends of the first and second crown strap portions being directly attached to one another and to an end of the top strap,
wherein the first and second crown strap portions cooperate to form a round shape or halo that is adapted to accommodate a crown of a patient's head, and
wherein, in a flat, pre-assembled state, the one-piece first cross strap and the one-piece second cross strap are each straight along their entire length.

10. The headgear according to claim 9, wherein the first and second crown strap portions are shorter than the first and second bottom strap portions.

11. The headgear according to claim 9, wherein the top strap, first cross strap, and second cross strap are constructed from a substantially flat or 2-dimensional piece of material, and attached to one another to achieve a 3-dimensional form.

12. Headgear for use with a mask assembly, consisting essentially of:
a top strap configured to extend over a top of a patient's head;
a one-piece bottom strap section including bottom straps and a first connector; and
a one-piece crown strap section including a pair of crown straps and a second connector attached to the first connector, the crown straps cooperating to form a round shape or halo that is adapted to accommodate a crown of a patient's head, each crown strap including a first end, the first ends of the crown straps being directly attached to one another and to a first end of the top strap, a second end of the top strap being configured to attach to a mask assembly,
wherein, in a flat, pre-assembled state, the crown straps each extend straight from the second connector to the respective first ends of the crown straps.

13. The headgear according to claim 12, wherein the bottom straps are configured to extend below a respective one of the patient's ears to connect to the mask assembly.

14. The headgear according to claim 12, wherein the connector of the one-piece bottom strap section extends between the bottom straps.

15. The headgear according to claim 12, wherein the connector of the one-piece crown strap section extends between the crown straps.

16. The headgear according to claim 12, wherein the top strap, bottom strap section, and crown strap section are constructed from a substantially flat or 2-dimensional piece of material, and attached to one another to achieve a 3-dimensional form.

17. Headgear for use with a mask assembly, comprising:
a top strap;
a bottom strap section including bottom straps and a connector; and
a crown strap section including a pair of crown straps and a connector attached to the connector of the bottom strap section, the crown straps cooperating to form a round shape or halo that is adapted to accommodate a crown of a patient's head, each crown strap including a first end, the first ends of the crown straps being directly attached to one another and to a first end of the top strap, a second end of the top strap being configured to attach to a mask assembly,
wherein each of the bottom strap section and the crown strap section is integrally formed from one piece of material and the bottom strap section and the crown strap section are wide angle V-shapes with substantially the same angle.

18. A method for forming headgear for a mask assembly, the method comprising:
forming a one-piece bottom strap section including bottom straps and a first connector;
forming a one-piece crown strap section including a pair of crown straps and a second connector, each crown strap including a first end;
forming a top strap;
attaching the first connector to the second connector;
attaching the first ends of the crown straps directly to one another so that the crown straps cooperate to form a round shape or halo that is adapted to accommodate a crown of a patient's head; and
attaching a first end of the top strap to the first ends of the crown straps, a second end of the top strap being configured to attach to a mask assembly,
wherein, in a flat, pre-assembled state, the crown straps each extend straight from the second connector to the respective first ends of the crown straps.

19. The method according to claim 18, wherein forming a bottom strap section and/or forming a crown strap section includes forming multiple sections from the single piece of material in a nesting arrangement.

20. A method for forming headgear for a mask assembly, the method comprising:
forming a one-piece first strap section including a first crown strap, a first bottom strap, and a first connector;
forming a one-piece second strap section including a second crown strap, a second bottom strap, and a second connector;
forming a top strap;
attaching the first connector to the second connector;
attaching ends of the first and second crown straps directly to one another so that the first and second crown straps cooperate to form a round shape or halo that is adapted to accommodate a crown of a patient's head; and
attaching an end of the top strap to the ends of the first and second, crown straps,
wherein, in a flat, pre-assembled state, the first crown strap extends straight from the first connector to the end of the first crown strap and the second crown strap extends straight from the second connector to the end of the second crown strap.

21. The method according to claim 20, wherein forming a first strap section and/or forming a second strap section includes forming multiple sections from the single piece of material in a nesting arrangement.

22. A method for forming headgear for a mask assembly, the method comprising:
forming a one-piece first cross strap including a first crown strap portion, a first bottom strap portion, and a first connector portion, forming a one-piece second cross strap including a second crown strap portion, a second bottom strap portion, and a second connector portion;
forming a top strap;
attaching the first connector portion to the second connector portion so that the first and second cross straps extend transverse to one another;
attaching ends of the first and second crown strap portions directly to one another so that the first and second crown strap portions cooperate to form a round shape or halo that is adapted to accommodate a crown of a patient's head; and
attaching an end of the top strap to the ends of the first and second crown strap portions,
wherein, in a flat, pre-assembled state, the one-piece first cross strap and the one-piece second cross strap are each straight along their entire length.

23. The method according to claim 22, wherein the first and second crown strap portions are shorter than the first and second bottom strap portions.

24. The method according to claim 22, wherein the top strap, first cross strap, and second cross strap are constructed from a substantially flat or 2-dimensional piece of material, and attached to one another to achieve a 3-dimensional form.

25. The method according to claim 22, wherein the top strap, first cross strap, and second cross strap are constructed from headgear material that provides up to about 14 mm of displacement for forces up to about 0.02 kN.

* * * * *